United States Patent
Brady-Kalnay

(10) Patent No.: US 12,013,397 B2
(45) Date of Patent: Jun. 18, 2024

(54) COMPOSITIONS AND METHODS FOR DETERMINING CANCER PROGNOSIS

(71) Applicant: CASE WESTERN RESERVE UNIVERSITY, Cleveland, OH (US)

(72) Inventor: Susann Brady-Kalnay, Cleveland, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 0 days.

(21) Appl. No.: 16/805,464

(22) Filed: Feb. 28, 2020

(65) Prior Publication Data
US 2020/0278350 A1    Sep. 3, 2020

Related U.S. Application Data

(60) Provisional application No. 62/811,792, filed on Feb. 28, 2019.

(51) Int. Cl.
    *G01N 33/00*      (2006.01)
    *G01N 33/574*      (2006.01)

(52) U.S. Cl.
    CPC ............... *G01N 33/57488* (2013.01)

(58) Field of Classification Search
CPC ... G01N 33/57488; G01N 2333/70503; G01N 2800/52
See application file for complete search history.

(56) References Cited

U.S. PATENT DOCUMENTS 8,686,112 B2     4/2014    Brady-Kalnay

FOREIGN PATENT DOCUMENTS

WO     WO2010019884    *   2/2010

OTHER PUBLICATIONS

Burden-Gulley et al (Neoplasia 12:305-316, 2010 (Year: 2010).*
Yan et al (NEJM 360:765-73, 2009 (Year: 2009).*
Brain tumor treatment Cancer.net Publication (Aug. 2009) (Year: 2009).*
Johansen, et al. "A PTPmu Biomarker is Associated with Increased Survival in Gliomas" Int. J. Mol. Sci. 2019, 20, 2372; doi:10.3390/ijms20102372, Published May 14, 2019.
Burden-Gulley, et al. "Molecular Magnetic Resonance Imaging of Tumors with a PTPμ Targeted Contrast Agent" Translational Oncology, vol. 6, No. 3, Jun. 2013, pp. 329-337.

* cited by examiner

*Primary Examiner* — Lei Yao
(74) *Attorney, Agent, or Firm* — TAROLLI, SUNDHEIM, COVELL & TUMMINO, LLP

(57) ABSTRACT

A method of determining a prognosis for cancer in a subject and/or a subject with cancer includes measuring a level of proteolytically cleaved extracellular fragments of an immunoglobulin (Ig) superfamily cell adhesion molecule that is expressed by cancer cells obtained from the subject to determine at least one of prognosis for the cancer, the subject's survival, or responsiveness of the cancer to anticancer treatment.

9 Claims, 12 Drawing Sheets

Specification includes a Sequence Listing.

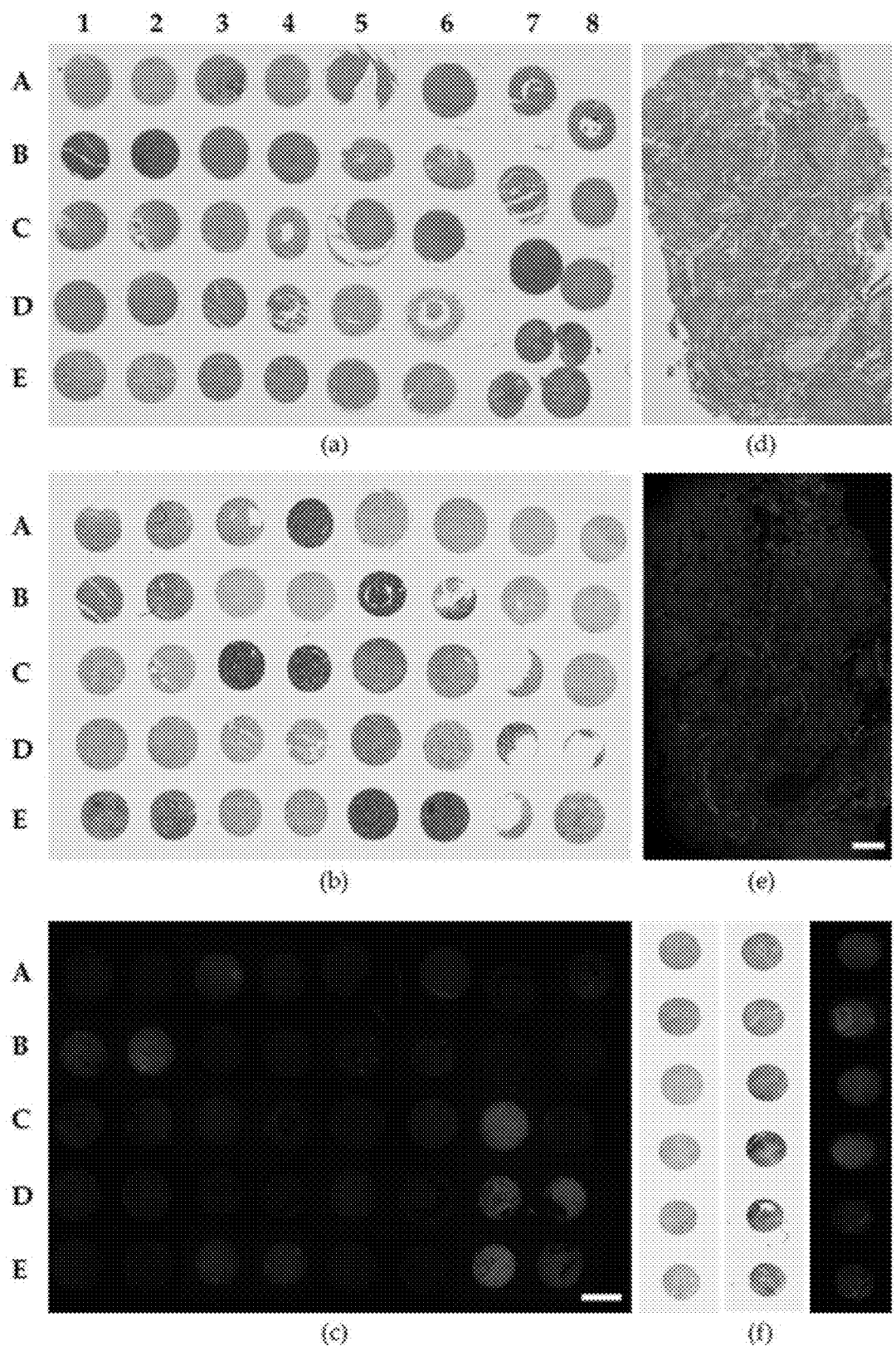
Figs. 1A-F (a: unadjusted survival of GBM patients)

(b: GBM survival adjusted)

(c: unadjusted recurrence free survival)

(d: GBM recurrence adjusted)

COMPOSITIONS AND METHODS FOR DETERMINING CANCER PROGNOSIS

RELATED APPLICATION

This application claims priority from U.S. Provisional Application No. 62/811,792 filed Feb. 28, 2019, the subject matter of which is incorporated herein by reference in its entirety.

BACKGROUND

Diffuse gliomas are malignant brain tumors that consist of astrocytomas, oligodendrogliomas, and glioblastomas. They represent approximately 70% of all malignant brain tumors, and range from low grade (WHO grade II) astrocytomas and oligodendrogliomas, to high grade (WHO grade III) astrocytomas and oligodendrogliomas, as well as glioblastomas (GBM, WHO grade IV). Low-grade diffuse gliomas have the best prognosis, with an overall survival of 11 years, whereas the overall survival for the most aggressive glioma, type IV GBM is only 15 months.

Treatment of low-grade glioma generally consists of debulking surgery, radiation therapy, and sometimes adjuvant chemotherapy. Treatment of grade III and IV gliomas consists of surgical resection, followed by radiation and chemotherapy, with extent of surgical resection being a major predictor of disease outcome. Conventional surgery has relied heavily upon the neurosurgeon's professional experience to recognize tumor from normal brain tissue, but more sophisticated approaches using magnetic resonance imaging (MRI) and/or fluorescent agents that identify tumor tissue are in use or development. Currently, one fluorescent agent, 5-aminolevulinic acid (5-ALA) is FDA approved to aid in the surgical resection of high grade (Grades III-IV) glioma. It is a non-specific agent that is metabolized preferentially but not exclusively in glioma tissue, and while helpful at improving extent of surgical resection, it lacks specificity in identifying tumor margins.

The World Health Organization (WHO) Classification of Tumors of the Central Nervous System introduced a new "integrated" scheme using molecular markers alongside traditional histopathology to classify diffuse gliomas. These recommendations include tests for mutated isocitrate dehydrogenase 1 (IDH1) status to differentiate tumors.

SUMMARY

Embodiments described herein relate to a method of determining a prognosis of cancer in a subject and/or a subject with cancer. It was found that the expression level of proteolytically cleaved extracellular fragments of an immunoglobulin (Ig) superfamily cell adhesion molecule, such as PTPμ, of cancer samples obtained from a subject correlated with cancer prognosis and/or survival of glioma patients including those with glioblastoma. Accordingly, the determination of the level of proteolytically cleaved extracellular fragments of an immunoglobulin (Ig) superfamily cell adhesion molecule that is expressed by cancer cells obtained from the subject can be used to determine at least one of prognosis for the cancer, the subject's survival, or responsiveness of the cancer to anti-cancer treatment In some embodiments, the level of proteolytically cleaved extracellular fragments can be determined by measuring a binding level of a probe to the proteolytically cleaved extracellular fragments of an immunoglobulin (Ig) superfamily cell adhesion molecule that is expressed by cancer cells. The cell adhesion molecule can include a cell surface receptor protein tyrosine phosphatase (PTP) type IIb, such as PTPμ or a PTPμ like molecule. The cancer cells can be, for example, brain cancer cells (e.g., surgical resection of brain tumor, glioma, high grade glioma (HGG), glioblastoma, or glioblastoma multiforme (GBM)), lung cancer cells, breast cancer cells, prostate cancer cells, melanoma cancer cells, ovarian cancer cells, endometrial cancer cells, oral cancer cells, and metastatic cancer cells.

In other embodiments, the extracellular fragment can have an amino acid sequence corresponding to amino acids 1-740 of SEQ ID NO: 1 and the probe can include a polypeptide that specifically binds to and/or complexes with amino acids 1-740 of SEQ ID NO: 1. In a further embodiment, the polypeptide can bind to homophilic binding domains or portions of an extracellular fragment of PTPμ, such as SEQ ID NO: 3, which comprises the MAM, Ig and first two FNIII repeat binding domain of PTPμ.

In yet another embodiment, the targeting agent can include a polypeptide having an amino acid sequence that has at least about 80%, about 90%, about 95%, about 96%, about 97%, about 98%, or about 99% sequence identity to about 10 to about 50 consecutive amino acids of the amino acid sequence of SEQ ID NO: 3. Examples of polypeptides having an amino acid sequence with an at least about 80% sequence identity to SEQ ID NO: 3 can be polypeptides having an amino acid sequence selected from the group consisting of SEQ ID NO: 4, SEQ ID NO: 5, SEQ ID NO: 6, and SEQ ID NO: 7.

In other embodiments, the probe can include a detectable label that is detectable by spectroscopic, photochemical, biochemical, immunochemical, electrical, optical, chemical, or similar methods. The detectable label can include, for example, at least one of ligands, radiolabels, fluorescent agents and dyes, infrared and near infrared agents, chemiluminescent agents, microparticles or nanoparticles, enzymes, colorimetric labels, magnetic labels, and chelating agents.

In some embodiments, the determined level indicates or correlates with a less or more favorable prognosis for the cancer. For example, an elevated determined level compared to a control can be indicative of an increased likelihood of survival of the subject and a decreased level is indicative of an increased likelihood of death of the subject.

In another embodiment, the method can further include determining the presence or level of at least one additional biomarker that indicates or correlates with at least one of prognosis for the cancer, the subject's survival, or responsiveness of the cancer to anti-cancer treatment. For example, the presence of a mutation in IDH1/2 expressed by the cancer can be determined, wherein the presence of the IDH1/2 mutations is indicative of increased likelihood of survival of the subject.

Other embodiments described herein relate to a method of determining survival of a subject with cancer. The method can include measuring a level of binding of a probe to proteolytically cleaved extracellular fragments of an immunoglobulin (Ig) superfamily cell adhesion molecule that is expressed by cancer cells obtained from the subject. The determined level can indicate or correlate with the subject's survival. In some embodiments, the cancer can be a brain tumor, glioma, high grade glioma (HGG), glioblastoma, or glioblastoma multiforme (GBM), and an elevated level of cancer cells compared to a control can be indicative of an increased likelihood of survival of the subject and a decreased level is indicative of an increased likelihood of death of the subject.

Optionally, the method can further include determining the presence of a mutation in IDH1/2 expressed by the cancer, wherein the presence of the of an IDH1/2 mutations is indicative of increased likelihood of survival of the subject.

BRIEF DESCRIPTION OF THE DRAWINGS

FIGS. 1(A-F) illustrate images showing staining for the PTPμ biomarker and mutant IDH1. This is a representative example of a TMA (A-C) or an individual slide (D-E) stained with the relevant markers. The patient samples are marked in rows A-E with numbers at the top from 1-8. Therefore, the tumor core location is referred to as A1, A2, etc. (A) H&E stain of the TMA. (B) mutant IDH1 staining of the TMA. (C) SBK4-TR stain of the TMA. (D) H&E of individual sample of GBM. (E) SBK4-TR stain of the same individual. Panel (F) shows a magnified image of the box in panel (C).

DETAILED DESCRIPTION

Figure 2A:
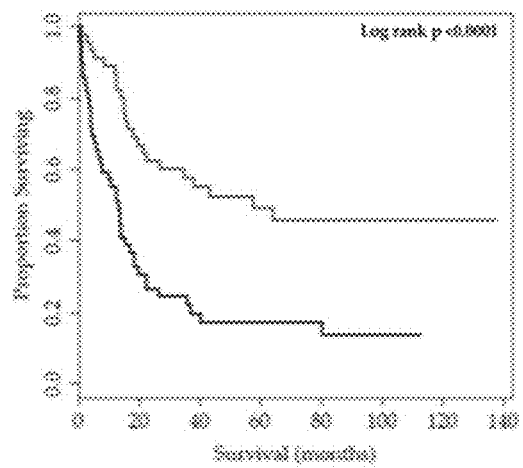
FIGS. 2(A-B) illustrate Kaplan Meier Plots for overall survival by PTPμ high versus low staining for all glioma patients. (A) Unadjusted overall survival. (B) Overall survival adjusted by sex, tumor grade, age group, and IDH1 mutation status. Median survival with 95% Confidence Intervals for each group are shown below each plot.

Methods involving conventional molecular biology techniques are described herein. Such techniques are generally known in the art and are described in detail in methodology treatises, such as *Current Protocols in Molecular Biology*, ed. Ausubel et al., Greene Publishing and Wiley-Interscience, New York, 1992 (with periodic updates). Unless otherwise defined, all technical terms used herein have the same meaning as commonly understood by one of ordinary skill in the art to which the application pertains. Commonly understood definitions of molecular biology terms can be found in, for example, Rieger et al., *Glossary of Genetics: Classical and Molecular*, 5th Edition, Springer-Verlag: New York, 1991, and Lewin, *Genes V*, Oxford University Press: New York, 1994.

The articles "a" and "an" are used herein to refer to one or to more than one (i.e., to at least one) of the grammatical object of the article. By way of example, "an element" means one element or more than one element.

The terms "comprise," "comprising," "include," "including," "have," and "having" are used in the inclusive, open sense, meaning that additional elements may be included. The terms "such as", "e.g.", as used herein are non-limiting and are for illustrative purposes only. "Including" and "including but not limited to" are used interchangeably.

The term "or" as used herein should be understood to mean "and/or", unless the context clearly indicates otherwise.

The term "agent" is used herein to denote a chemical compound, a mixture of chemical compounds, a biological macromolecule, or an extract made from biological materials.

The terms "antibody" or "antibody peptide(s)" refer to an intact antibody, or a binding fragment thereof that competes with the intact antibody for specific binding. Binding fragments are produced by recombinant DNA techniques, or by enzymatic or chemical cleavage of intact antibodies. Binding fragments include Fab, Fab', F(ab')$_2$, Fv, and single-chain antibodies. An antibody other than a "bispecific" or "bifunctional" antibody is understood to have each of its binding sites identical.

The terms "cancer" or "tumor" refer to any neoplastic growth in a subject, including an initial tumor and any metastases. The cancer can be of the liquid or solid tumor type. Liquid tumors include tumors of hematological origin, including, e.g., myelomas (e.g., multiple myeloma), leukemias (e.g., Waldenstrom's syndrome, chronic lymphocytic leukemia, other leukemias), and lymphomas (e.g., B-cell lymphomas, non-Hodgkin's lymphoma). Solid tumors can originate in organs and include cancers of the lungs, brain, breasts, prostate, ovaries, colon, kidneys and liver.

By "aggressiveness" and "aggressive" is meant a property or propensity for a cancer to have a relatively poor prognosis due to one or more of a combination of features or factors including: at least partial resistance to therapies available for cancer treatment; invasiveness; metastatic potential; recurrence after treatment; and a low probability of patient survival, although without limitation thereto.

Cancers may include any aggressive or potentially aggressive cancers, tumors or other malignancies such as listed in the NCI Cancer Index including all major cancer forms, such as sarcomas, carcinomas, lymphomas, leukemias, and blastomas, although without limitation thereto. These may include breast cancer, lung cancer inclusive of lung adenocarcinoma and mesothelioma, cancers of the reproductive system inclusive of ovarian cancer, cervical cancer, uterine cancer and prostate cancer, cancers of the brain and nervous system, head and neck cancers, gastrointestinal cancers inclusive of colon cancer, colorectal cancer and gastric cancer, liver cancer, kidney cancer, skin cancers such as melanoma and skin carcinomas, blood cell cancers inclusive of lymphoid cancers and myelomonocytic cancers, cancers of the endocrine system such as pancreatic cancer and pituitary cancers, musculoskeletal cancers inclusive of bone and soft tissue cancers, although without limitation thereto.

In particular embodiments, the cancer includes breast cancer, lung cancer, ovarian cancer, cervical cancer, uterine cancer, prostate cancer, cancer of the brain and nervous system, head and neck cancer, colon cancer, colorectal cancer, gastric cancer, liver cancer, kidney cancer, bladder cancer, skin cancer, pancreatic cancer, pituitary cancer or adrenal cancer.

In further embodiments, the cancer includes brain cancer, lung cancers, breast cancer, prostate cancer, melanoma cancer, ovarian cancer, endometrial cancer, oral cancer, and metastatic cancer.

The term "epitope" includes any protein determinant capable of specific binding to an immunoglobulin. Epitope determinants usually consist of chemically active surface groupings of molecules such as amino acids or sugar side chains and usually have specific three-dimensional structural characteristics, as well as specific charge characteristics.

The term "gene" or "recombinant gene" refers to a nucleic acid comprising an open reading frame encoding a polypeptide, including both exon and (optionally) intron sequences.

The term "homology" and "identity" are used synonymously throughout and refer to sequence similarity between two peptides or between two nucleic acid molecules. Homology can be determined by comparing a position in each sequence, which may be aligned for purposes of comparison. When a position in the compared sequence is occupied by the same base or amino acid, then the molecules are homologous or identical at that position. A degree of homology or identity between sequences is a function of the number of matching or homologous positions shared by the sequences.

The term "monoclonal" refers to an antibody that specifically binds to a sequence of amino acid and/or a specific epitope of an antigen.

The term "mutant" refers to any change in the genetic material of an organism, in particular a change (i.e., deletion, substitution, addition, or alteration) in a wild type polynucleotide sequence or any change in a wild type protein. The term "variant" is used interchangeably with "mutant". Although it is often assumed that a change in the genetic material results in a change of the function of the protein, the terms "mutant" and "variant" refer to a change in the sequence of a wild type protein regardless of whether that change alters the function of the protein (e.g., increases, decreases, imparts a new function), or whether that change has no effect on the function of the protein (e.g., the mutation or variation is silent).

The term "nanoparticle" refers to any particle having a diameter of less than 1000 nanometers (nm). In some embodiments, nanoparticles can be optically or magnetically detectable. In some embodiments, intrinsically fluorescent or luminescent nanoparticles, nanoparticles that comprise fluorescent or luminescent moieties, plasmon resonant nanoparticles, and magnetic nanoparticles are among the detectable nanoparticles that are used in various embodiments. In general, the nanoparticles should have dimensions small enough to allow their uptake by eukaryotic cells. Typically the nanoparticles have a longest straight dimension (e.g., diameter) of 200 nm or less. In some embodiments, the nanoparticles have a diameter of 100 nm or less. Smaller nanoparticles, e.g., having diameters of 50 nm or less, e.g., about 1 nm to about 30 nm or about 1 nm to about 5 nm, are used in some embodiments.

The term "nucleic acid" refers to polynucleotides, such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides.

The terms "patient", "subject", "mammalian host," and the like are used interchangeably herein, and refer to mammals, including human and veterinary subjects.

The terms "peptide(s)", "protein(s)" and "polypeptide(s)" are used interchangeably herein. As used herein, "polypeptide" refers to any peptide or protein comprising two or more amino acids joined to each other by peptide bonds or modified peptide bonds (i.e., peptide isomers). "Polypeptide(s)" refers to both short chains, commonly referred as peptides, oligopeptides or oligomers, and to longer chains generally referred to as proteins.

The terms "polynucleotide sequence" and "nucleotide sequence" are also used interchangeably herein.

"Recombinant," as used herein, means that a protein is derived from a prokaryotic or eukaryotic expression system.

The term "wild type" refers to the naturally-occurring polynucleotide sequence encoding a protein, or a portion thereof, or protein sequence, or portion thereof, respectively, as it normally exists in vivo.

Throughout the description, where compositions are described as having, including, or comprising, specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the compositions and methods described herein remains operable. Moreover, two or more steps or actions can be conducted simultaneously.

Embodiments described herein relate to a method of determining a prognosis of cancer in a subject and/or a subject with cancer by measuring the level of proteolytically cleaved extracellular fragments of an immunoglobulin (Ig) superfamily cell adhesion molecule, such as protein tyrosine phosphatase (PTP) type IIb (e.g., PTPμ or a PTPμ like molecule) that is expressed by cancer cells obtained from a subject and, optionally, determining gene and/or protein expression levels of an additional one or plurality of biomarkers of cancer prognosis.

In some embodiments, the prognosis determined by measuring the level of proteolytically cleaved extracellular fragments of an Ig superfamily cell adhesion molecule that is expressed by cancer cells obtained from the subject can be used for at least one of determining the prognosis for the cancer (e.g., for predicting a clinical outcome (with or without medical treatment), determining responsiveness to anti-cancer treatment (e.g., for selecting an appropriate course of treatment (or whether treatment would be effective) and/or monitoring a current treatment and potentially changing the treatment), and/or determining the subject's survival.

The prognosis may also include a prediction, forecast or anticipation of any lasting or permanent physical or psychological effects of cancer suffered by the subject after the cancer has been successfully treated or otherwise resolved. Furthermore, prognosis may include one or more of determining metastatic potential or occurrence, therapeutic responsiveness to anti-cancer treatment, implementing appropriate treatment regimes, determining the probability, likelihood or potential for cancer recurrence after therapy and prediction of development of resistance to established therapies (e.g., chemotherapy). It would be appreciated that a positive prognosis typically refers to a beneficial clinical outcome or outlook, such as increased likelihood of survival or long-term survival without recurrence of the subject's cancer, whereas a negative prognosis typically refers to a negative clinical outcome or outlook, such as cancer recurrence or progression or increased likelihood of death of the subject.

In one embodiment of the method, a relatively increased measured level of proteolytically cleaved extracellular fragments of an immunoglobulin (Ig) superfamily cell adhesion molecule indicates or correlates with a more favorable prognosis and/or a less aggressive cancer; and/or a relatively decreased measured level of proteolytically cleaved extracellular fragments of an immunoglobulin (Ig) superfamily cell adhesion molecule indicates or correlates with a less favorable prognosis and/or a highly aggressive cancer.

In another embodiment, the cancer prognosis is used, at least in part, to determine whether the subject would benefit from treatment of the cancer. By way of example, a patient with a favorable prognosis and/or a less aggressive cancer may be less likely to suffer from rapid local progression of the cancer and/or metastasis and can be spared from more aggressive monitoring and/or therapy.

In another embodiment, the cancer prognosis can be used, at least in part, to develop a treatment strategy for the subject.

In another embodiment, the cancer prognosis can be used, at least in part, to determine disease progression or recurrence in the subject.

In yet another embodiment, the cancer prognosis or aggressiveness can be used, at least in part, to determine an estimated time of survival.

In some embodiments, the level of proteolytically cleaved extracellular fragments can be determined by measuring a binding level of a probe to the proteolytically cleaved extracellular fragments of an Ig superfamily cell adhesion molecule that is expressed by cancer cells obtained from the subject. It was found that probes, that can specifically bind to and/or complex with these proteolytically cleaved extracellular fragments or segments in cancer samples, such as cancer cells, obtained from a subject can be used for determining at least one of prognosis for the cancer, the subject's survival, or responsiveness of the cancer to anti-cancer treatment.

The Ig superfamily cell adhesion molecule can include receptor protein tyrosine phosphatases (RPTP) type IIb cell adhesion molecules. In another example, Ig superfamily cell adhesion molecules can include RPTPs of the PTPµ-like subfamily, such as PTPµ, PTPκ, PTPρ, and PCP-2 (also called PTPλ). PTPµ-like RPTPs include a MAM (Meprin/A5-protein/PTPµ) domain, an Ig domain, and FNIII repeats. PTPµ can have the amino acid sequence of SEQ ID NO: 1, which is identified by Genbank Accession No. AAI51843.1. It will be appreciated that the PTPµ gene can generate splice variants such that the amino acid sequence of PTPµ can differ from SEQ ID NO: 1. In some embodiments, PTPµ can have an amino acid sequence identified by Genbank Accession No. AAH51651.1 and Genbank Accession No. AAH40543.1.

In some embodiments, the probe that is used to determine the level of the extracellular fragment of the proteolytically cleaved extracellular fragment of the Ig superfamily cell adhesion molecule that engages in homophilic binding can include a targeting agent that specifically binds to and/or complexes with the proteolytically cleaved extracellular fragment of the Ig superfamily cell adhesion molecule of the cancer cell. The targeting agent can include a targeting small molecule, polypeptide, or antibody or a fragment of an antibody that binds to and/or complexes with the proteolytically cleaved extracellular fragment of the Ig superfamily cell adhesion molecule.

In some embodiments, the targeting agent can include a polypeptide (or targeting polypeptide) that binds to and/or complexes with the proteolytically cleaved extracellular fragment of the Ig superfamily cell adhesion molecule. The targeting polypeptide can include, consist essentially of, or consist of about 10 to about 50 amino acids and have an amino acid sequence that is substantially homologous to about 10 to about 50 consecutive amino acids of a homophilic binding portion or domain of the proteolytically cleaved extracellular fragment of the Ig superfamily cell adhesion molecule. By substantially homologous, it is meant the targeting polypeptide has at least about 80%, about 90%, about 95%, about 96%, about 97%, about 98%, about 99% or about 100% sequence identity with a portion of the amino acid sequence of the binding portion of the proteolytically cleaved extracellular fragment of the Ig superfamily cell adhesion molecule.

In one example, the homophilic binding portion of the Ig superfamily cell adhesion molecule can include, for example, the Ig domain of the cell adhesion molecule. In another example, where the Ig superfamily cell adhesion molecule is PTPµ, the homophilic binding portion can include the Ig binding domain and the MAM domain.

In another aspect, the targeting polypeptide can have an amino acid sequence that is substantially homologous to about 10 to about 50 consecutive amino acids of the Ig binding domain and/or MAM domain of PTPµ (e.g., SEQ ID NO: 1), such as amino acids 1-740 of SEQ ID NO: 1.

In some embodiments, the proteolytically cleaved extracellular fragment of PTPµ can include an amino acid sequence of any component of the extracellular domain contained within SEQ ID NO: 1 or its receptor. In other embodiments, the proteolytically cleaved extracellular fragment of PTPµ can include an amino acid sequence of SEQ ID NO: 2, the Ig and MAM binding region can comprise the amino acid sequence of SEQ ID NO: 3, and the polypeptide can have an amino acid sequence that is substantially homologous to about 10 to about 50 consecutive amino acids of SEQ ID NO: 2 or SEQ ID NO: 3. Examples of polypeptides that can specifically bind SEQ ID NO: 2 or SEQ ID NO: 3 and have an amino acid sequence that is substantially homologous to about 10 to about 50 consecutive amino acids of SEQ ID NO: 2 or SEQ ID NO: 3 are polypeptides that comprising an amino acid sequence selected from the group consisting of SEQ ID NO: 4 (SBK1), SEQ ID NO: 5 (SBK2), SEQ ID NO: 6 (SBK3), and SEQ ID NO: 7 (SBK4). Polypeptides comprising SEQ ID NO: 4, 5, 6, or 7 can recognize or bind to the MAM (SBK1 and SBK2), Ig domain (SBK3 and SBK4), or the FNIII repeats.

In other embodiments, a polypeptide that binds to and/or complexes with the proteolytically cleaved extracellular fragment of the Ig superfamily CAM or its receptor that is expressed by a cancer cell or another cell in the cancer cell microenvironment can have an amino acid sequence of SEQ ID NO: 8. SEQ ID NO: 8 is substantially homologous to a portion of SEQ ID NO: 1 or SEQ ID NO: 2 and can specifically bind to SEQ ID NO: 2 or SEQ ID NO: 3.

The targeting polypeptides can be subject to various changes, substitutions, insertions, and deletions where such changes provide for certain advantages in its use. In this regard, targeting peptides that bind to and/or complex with a proteolytically cleaved extracellular portion of an Ig superfamily cell adhesion molecule can be substantially homologous with, rather than be identical to, the sequence of a recited polypeptide where one or more changes are made and it retains the ability to function as specifically binding to and/or complexing with the proteolytically cleaved extracellular portion of an Ig superfamily cell adhesion molecule.

The targeting peptides can be in any of a variety of forms of polypeptide derivatives, that include amides, conjugates with proteins, cyclized polypeptides, polymerized polypeptides, retro-inverso peptides, analogs, fragments, chemically modified polypeptides, and the like derivatives.

Retro-inverso peptides are linear peptides whose amino acid sequence is reversed and the α-center chirality of the amino acid subunits is inverted as well. These types of peptides are designed by including D-amino acids in the reverse sequence to help maintain side chain topology similar to that of the original L-amino acid peptide and make them more resistant to proteolytic degradation. D-amino acids represent conformational mirror images of natural L-amino acids occurring in natural proteins present in biological systems. Peptides that contain D-amino acids have advantages over peptides that just contain L-amino acids. In general, these types of peptides are less susceptible to proteolytic degradation and have a longer effective time when used as pharmaceuticals. Furthermore, the insertion of D-amino acids in selected sequence regions as sequence blocks containing only D-amino acids or in-between L-amino acids allows the design of peptide based drugs that are bioactive and possess increased bioavailability in addition to being resistant to proteolysis. Furthermore, if properly designed, retro-inverso peptides can have binding characteristics similar to L-peptides.

The term "analog" includes any polypeptide having an amino acid residue sequence substantially identical to a sequence specifically shown herein in which one or more residues have been conservatively substituted with a functionally similar residue and that specifically binds to and/or complexes with the proteolytically cleaved extracellular portion of an Ig superfamily CAM as described herein. Examples of conservative substitutions include the substitution of one non-polar (hydrophobic) residue, such as isoleucine, valine, leucine or methionine for another, the substitution of one polar (hydrophilic) residue for another, such as between arginine and lysine, between glutamine and asparagine, between glycine and serine, the substitution of one basic residue such as lysine, arginine or histidine for another, or the substitution of one acidic residue, such as aspartic acid or glutamic acid for another.

The phrase "conservative substitution" also includes the use of a chemically derivatized residue in place of a non-derivatized residue provided that such peptide displays the requisite binding activity.

"Chemical derivative" refers to a subject polypeptide having one or more residues chemically derivatized by reaction of a functional side group. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those polypeptides, which contain one or more naturally occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine. Polypeptides described herein also include any polypeptide having one or more additions and/or deletions or residues relative to the sequence of a polypeptide whose sequence is shown herein, so long as the requisite activity is maintained.

The term "fragment" refers to any subject polypeptide having an amino acid residue sequence shorter than that of a polypeptide whose amino acid residue sequence is shown herein.

Additional residues may also be added at either terminus of a polypeptide for the purpose of providing a "linker" by which the polypeptides can be conveniently linked and/or affixed to other polypeptides, proteins, detectable moieties, labels, solid matrices, or carriers.

Amino acid residue linkers are usually at least one residue and can be 40 or more residues, more often 1 to 10 residues. Typical amino acid residues used for linking are glycine, tyrosine, cysteine, lysine, glutamic and aspartic acid, or the like. For example, SBK2 (SEQ ID NO: 5) can include a linker with three glycine residue (SEQ ID NO: 9), six glycine residues (SEQ ID NO: 10), and combinations of glycine and serine residues (SEQ ID NO: 11 and SEQ ID NO: 12). Similarly, SBK4 (SEQ ID NO: 7) can include a linker with three glycine residue (SEQ ID NO: 13), six glycine residues (SEQ ID NO: 14), and combinations of glycine and serine residues (SEQ ID NO: 15 and SEQ ID NO: 16).

In addition, a subject polypeptide can differ by the sequence being modified by terminal-NH2 acylation, e.g., acetylation, or thioglycolic acid amidation, by terminal-carboxylamidation, e.g., with ammonia, methylamine, and the like terminal modifications. Terminal modifications are useful, as is well known, to reduce susceptibility by proteinase digestion, and therefore serve to prolong half-life of the polypeptides in solutions, particularly biological fluids where proteases may be present. In this regard, polypeptide cyclization is also a useful terminal modification, and is particularly preferred also because of the stable structures formed by cyclization and in view of the biological activities observed for such cyclic peptides as described herein.

In some embodiments, the linker can be a flexible peptide linker that links the therapeutic peptide to other polypeptides, proteins, and/or molecules, such as detectable moieties, labels, solid matrices, or carriers. A flexible peptide linker can be about 20 or fewer amino acids in length. For example, a peptide linker can contain about 12 or fewer amino acid residues, e.g., 1, 2, 3, 4, 5, 6, 7, 8, 9, 10, 11, and 12. In some cases, a peptide linker comprises two or more of the following amino acids: glycine, serine, alanine, and threonine.

Any polypeptide or compound may also be used in the form of a pharmaceutically acceptable salt. Acids, which are capable of forming salts with the polypeptides, include inorganic acids such as trifluoroacetic acid (TFA) hydrochloric acid (HCl), hydrobromic acid, perchloric acid, nitric acid, thiocyanic acid, sulfuric acid, phosphoric acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid or the like.

Bases capable of forming salts with the polypeptides include inorganic bases such as sodium hydroxide, ammonium hydroxide, potassium hydroxide and the like; and organic bases such as mono-, di- and tri-alkyl and arylamines (e.g., triethylamine, diisopropylamine, methylamine, dimethylamine and the like) and optionally substituted ethanolamines (e.g., ethanolamine, diethanolamine and the like).

The targeting polypeptides can be synthesized by any of the techniques that are known to those skilled in the peptide art, including recombinant DNA techniques. Synthetic chemistry techniques, such as a solid-phase Merrifield-type synthesis, can be used for reasons of purity, antigenic specificity, freedom from undesired side products, ease of production and the like. A summary of the many techniques available can be found in Steward et al., "Solid Phase Peptide Synthesis", W. H. Freeman Co., San Francisco, 1969; B odanszky, et al., "Peptide Synthesis", John Wiley & Sons, Second Edition, 1976; J. Meienhofer, "Hormonal Proteins and Peptides", Vol. 2, p. 46, Academic Press (New York), 1983; Merrifield, Adv. Enzymol., 32:221-96, 1969; Fields et al., int. J. Peptide Protein Res., 35:161-214, 1990; and U.S. Pat. No. 4,244,946 for solid phase peptide synthesis, and Schroder et al., "The Peptides", Vol. 1, Academic Press (New York), 1965 for classical solution synthesis, each of which is incorporated herein by reference. Appropriate protective groups usable in such synthesis are described in the above texts and in J. F. W. McOmie, "Protective Groups in Organic Chemistry", Plenum Press, New York, 1973, which is incorporated herein by reference.

In general, the solid-phase synthesis methods contemplated comprise the sequential addition of one or more amino acid residues or suitably protected amino acid residues to a growing peptide chain. Normally, either the amino or carboxyl group of the first amino acid residue is protected by a suitable, selectively removable protecting group. A different, selectively removable protecting group is utilized for amino acids containing a reactive side group such as lysine.

Using a solid phase synthesis as an example, the protected or derivatized amino acid can be attached to an inert solid support through its unprotected carboxyl or amino group. The protecting group of the amino or carboxyl group can then be selectively removed and the next amino acid in the sequence having the complimentary (amino or carboxyl) group suitably protected is admixed and reacted under conditions suitable for forming the amide linkage with the residue already attached to the solid support. The protecting group of the amino or carboxyl group can then be removed from this newly added amino acid residue, and the next amino acid (suitably protected) is then added, and so forth. After all the desired amino acids have been linked in the proper sequence, any remaining terminal and side group protecting groups (and solid support) can be removed sequentially or concurrently, to afford the final linear polypeptide.

Furthermore, the targeting polypeptides can be used as a starting point to develop higher affinity small molecules, antibodies, and/or antibody fragments with similar ligand binding capabilities. The development and screening of small molecules from pharmacophores of the polypeptides using, for example, in silico screening, can be readily performed, and the binding affinity of such identified molecules can be readily screened against targeting polypeptides using assays described herein to select small molecule agents.

In other embodiments, the targeting agent that specifically binds to or complexes with a proteolytically cleaved extracellular fragment of an immunoglobulin (Ig) superfamily cell adhesion molecule that is expressed by cancer cells obtained from the subject can be an antibody, such as a monoclonal antibody, a polyclonal antibody, or a humanized antibody. The antibody can include Fc fragments, Fv fragments, single chain Fv (scFv) fragments, Fab' fragments, F(ab')2 fragments, single domain antibodies, camelized antibodies and other antibody fragments. The antibody can also include multivalent versions of the foregoing antibodies or fragments thereof including monospecific or bispecific antibodies, such as disulfide stabilized Fv fragments, scFv tandems ((scFv)$_2$ fragments), diabodies, tribodies or tetrabodies, which typically are covalently linked or otherwise stabilized (i.e., leucine zipper or helix stabilized) scFv fragments; and receptor molecules, which naturally interact with a desired target molecule.

In some embodiments the antibody or fragment thereof can specifically or selectively bind to either the full length protein or a proteolytically cleaved extracellular fragment of PTPμ having the amino acid sequence of SEQ ID NO: 2. In other embodiments, the antibody or fragment thereof can specifically bind to the Ig and MAM binding region having the amino acid sequence of SEQ ID NO: 3 of the proteolytically cleaved extracellular fragment of PTPμ. In still other embodiments, the antibody or fragment thereof can specifically bind to an amino acid sequence selected from the group consisting of SEQ ID NO: 4, SEQ ID NO: 5, SEQ ID NO: 6, and SEQ ID NO: 7.

Preparation of antibodies can be accomplished by any number of methods for generating antibodies. These methods typically include the step of immunization of animals, such as mice or rabbits, with a desired immunogen (e.g., a desired target molecule or fragment thereof). Once the mammals have been immunized, and boosted one or more times with the desired immunogen(s), antibody-producing hybridomas may be prepared and screened according to well known methods. See, for example, Kuby, Janis, Immunology, Third Edition, pp. 131-139, W.H. Freeman & Co. (1997), for a general overview of monoclonal antibody production, that portion of which is incorporated herein by reference.

In vitro methods that combine antibody recognition and phage display techniques can also be used to allow one to amplify and select antibodies with very specific binding capabilities. See, for example, Holt, L. J. et al., "The Use of Recombinant Antibodies in Proteomics," Current Opinion in Biotechnology, 2000, 11:445-449, incorporated herein by reference. These methods typically are much less cumbersome than preparation of hybridomas by traditional monoclonal antibody preparation methods.

In some embodiments, phage display technology may be used to generate an antibody or fragment thereof specific for a desired target molecule. An immune response to a selected immunogen is elicited in an animal (such as a mouse, rabbit, goat or other animal) and the response is boosted to expand the immunogen-specific B-cell population. Messenger RNA is isolated from those B-cells, or optionally a monoclonal or polyclonal hybridoma population. The mRNA is reverse-transcribed by known methods using either a poly-A primer or murine immunoglobulin-specific primer(s), typically specific to sequences adjacent to the desired $V_H$ and $V_L$ chains, to yield cDNA. The desired $V_H$ and $V_L$ chains are amplified by polymerase chain reaction (PCR) typically using $V_H$ and $V_L$ specific primer sets, and are ligated together, separated by a linker. $V_H$ and $V_L$ specific primer sets are commercially available, for instance from Stratagene, Inc. of La Jolla, Calif. Assembled $V_H$-linker-$V_L$ product (encoding a scFv fragment) is selected for and amplified by PCR. Restriction sites are introduced into the ends of the $V_H$-linker-$V_L$ product by PCR with primers including restriction sites and the scFv fragment is inserted into a suitable expression vector (typically a plasmid) for phage display. Other fragments, such as a Fab' fragment, may be cloned into phage display vectors for surface expression on phage particles. The phage may be any phage, such as lambda, but typically is a filamentous phage, such as Fd and M13, typically M13.

In phage display vectors, the $V_H$-linker-$V_L$ sequence is cloned into a phage surface protein (for M13, the surface proteins g3p (pIII) or g8p, most typically g3p). Phage display systems also include phagemid systems, which are based on a phagemid plasmid vector containing the phage surface protein genes (for example, g3p and g8p of M13) and the phage origin of replication. To produce phage particles, cells containing the phagemid are rescued with helper phage providing the remaining proteins needed for the generation of phage. Only the phagemid vector is packaged in the resulting phage particles because replication of the phagemid is grossly favored over replication of the helper phage DNA. Phagemid packaging systems for production of antibodies are commercially available. One example of a commercially available phagemid packaging system that also permits production of soluble ScFv fragments in bacterial cells is the Recombinant Phage Antibody System (RPAS), commercially available from Amersham Pharmacia Biotech, Inc. of Piscataway, N.J. and the pSKAN Phagemid Display System, commercially available from MoBiTec, LLC of Marco Island, Fla. Phage display systems, their construction, and screening methods are described in detail in, among others, U.S. Pat. Nos. 5,702,892, 5,750,373, 5,821,047 and 6,127,132, each of which is incorporated herein by reference in their entirety.

In other embodiments, the targeting agent can be directly or indirectly labeled with a detectable label. The role of a detectable label is to facilitate the detection step of a diagnostic method by allowing visualization of the complex formed by binding of the probe to the proteolytically cleaved extracellular fragment of the Ig superfamily cell adhesion molecule of the cancer cells obtained from the subject. The detectable label can be selected such that it generates a signal, which can be measured and whose intensity is related (preferably proportional) to the amount of the probe bound to the cancer cells being analyzed. Methods for labeling biological molecules, such as polypeptides and antibodies are well-known in the art.

Detectable labels can include any composition detectable by spectroscopic, photochemical, biochemical, immunochemical, electrical, optical, chemical or similar methods. Such labels include biotin for staining with labeled streptavidin conjugate, magnetic beads (e.g., DYNABEADS), fluorescent dyes (e.g., fluorescein, Texas red, rhodamine, green fluorescent protein, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and calorimetric labels such as colloidal gold or colored glass or plastic (e.g., polystyrene, polypropylene, latex, etc) beads. Patents teaching the use of such labels include U.S. Pat. Nos. 3,817,837; 3,850,752; 3,939,350; 3,996,345; 4,277,437; 4,275,149; and 4,366,241. Means of detecting such labels are well known to those of skill in the art. Thus, for example, radiolabels may be detected using photographic film or scintillation counters, fluorescent markers may be detected using a photodetector to detect emitted light. Enzymatic labels are typically detected by providing the enzyme with a substrate and detecting the reaction product produced by the action of the enzyme on the substrate, and calorimetric labels are detected by simply visualizing the colored label. Labels can include, e.g., ligands that bind to labeled antibodies, fluorophores, chemiluminescent agents, enzymes, and antibodies, which can serve as specific binding pair members for a labeled ligand. An introduction to labels, labeling procedures and detection of labels is found in Polak and Van Noorden Introduction to Immunocytochemistry, 2nd ed., Springer Verlag, N.Y. (1997); and in Haugland Handbook of Fluorescent Probes and Research Chemicals, a combined handbook and catalogue Published by Molecular Probes, Inc. (1996).

Detectable labels include, but are not limited to, nucleotides (labeled or unlabeled), compomers, sugars, peptides, proteins, antibodies, chemical compounds, conducting polymers, binding moieties such as biotin, mass tags, calorimetric agents, light emitting agents, chemiluminescent agents, light scattering agents, fluorescent tags, radioactive tags, charge tags (electrical or magnetic charge), volatile tags and hydrophobic tags, biomolecules (e.g., members of a binding pair antibody/antigen, antibody/antibody, antibody/antibody fragment, antibody/antibody receptor, antibody/protein A or protein G, hapten/anti-hapten, biotin/avidin, biotin/streptavidin, folic acid/folate binding protein, vitamin B12/intrinsic factor, chemical reactive group/complementary chemical reactive group (e.g., sulfhydryl/maleimide, sulfhydryl/haloacetyl derivative, amine/isotriocyanate, amine/succinimidyl ester, and amine/sulfonyl halides) and the like.

In other embodiments, the detectable label can include at least one of ligands, radiolabels, fluorescent agents and dyes, infrared and near infrared agents, chemiluminescent agents, microparticles or nanoparticles, enzymes, colorimetric labels, magnetic labels, and chelating agents.

In some embodiments, the detectable label can be linked to the targeting agent (e.g., polypeptide or antibody) via a linking molecule which is not a contiguous portion of either the polypeptide or antibody and which covalently joins an amino acid of the polypeptide or antibody to the detectable label. As used herein, a linking molecule that is "not a contiguous portion" means that the polypeptide or antibody and detectable label are connected via an additional element that is not a part of the polypeptide or antibody and functions as a linker.

In some embodiments, the linking molecule may be a peptide linker. Where the linker is a peptide linker. Alternatively, a linking molecule may be a non-peptide linker. As used herein, a non-peptide linker useful for the method described herein is a biocompatible polymer including two or more repeating units linked to each other. Examples of the non-peptide polymer include but are not limited to: polyethylene glycol (PEG), polypropylene glycol (PPG), co-poly (ethylene/propylene) glycol, polyoxyethylene (POE), polyurethane, polyphosphazene, polysaccharides, dextran, polyvinyl alcohol, polyvinylpyrrolidones, polyvinyl ethyl ether, polyacryl amide, polyacrylate, polycyanoacrylates, lipid polymers, chitins, hyaluronic acid, and heparin. For more detailed descriptions of non-peptide linkers useful for Fc fusion molecules, see, for example, WO/2006/107124, which is incorporated by reference herein. Typically such linkers will have a range of molecular weight of from about 1 kDa to 50 kDa, depending upon a particular linker. For example, a typical PEG has a molecular weight of about 1 to 5 kDa, and polyethylene glycol has a molecular weight of about 5 kDa to 50 kDa, and more preferably about 10 kDa to 40 kDa.

In some embodiments, the level of proteolytically cleaved extracellular fragments of an Ig superfamily cell adhesion molecule can be measured by applying a detectable quantity of the probe to a biological sample containing cancer cells obtained from the subject. The detectable quantity means can be an amount of the administered or applied probe that is sufficient to enable detection of binding level of the probe to the cancer cells.

The biological sample can include any sample that contains cancer cells. The biological sample can include sections of tissues such as biopsy or tissue removed during surgical or other procedures, bodily fluids, autopsy samples, and frozen sections taken for histological purposes. Such samples include blood and blood fractions or products (e.g., serum, buffy coat, plasma, platelets, red blood cells, and the like), sputum, malignant effusion, cheek cells tissue, cultured cells (e.g., primary cultures, explants, and transformed cells), stool, urine, other biological or bodily fluids (e.g., prostatic fluid, gastric fluid, intestinal fluid, renal fluid, lung fluid, cerebrospinal fluid, and the like), etc.

The biological sample can be an initial unprocessed sample taken from a subject or a subsequently processed sample, e.g., partially purified or preserved forms. In some embodiments, the biological sample may be a tissue sample, for example, a tissue sample obtained from a tumor site or a suspected tumor site (a tissue site suspected of containing cancer cells). In some embodiments, multiple (e.g., at least 2, 3, 4, 5, or more) biological samples may be collected from a subject, over time or at particular time intervals, for example to assess the disease progression or evaluate the efficacy of a treatment.

In some embodiments, the sample used in the methods described herein can be a formalin fixed paraffin embedded (FFPE) sample. The FFPE sample can be one or more of fixed tissue, unstained slides, core needle biopsy, and fine needle aspirate (FNA). In an embodiment, the fixed tissue comprises a tumor containing formalin fixed paraffin embedded (FFPE) block from a surgery or biopsy. In another embodiment, the unstained slides comprise unstained, charged, unbaked slides from a paraffin block. In still another embodiment, the core needle biopsy comprises 1, 2, 3, 4, 5, 6, 7, 8, 9, 10 or more, e.g., 3-4, paraffin embedded biopsy samples. An 18-gauge needle biopsy can be used.

A sample may be processed according to techniques understood by those in the art. A sample can be without limitation fresh, frozen or fixed cells or tissue. In some embodiments, a sample comprises formalin-fixed paraffin-embedded (FFPE) tissue, fresh tissue or fresh frozen (FF) tissue. A sample can comprise cultured cells, including primary or immortalized cell lines derived from a subject sample.

Samples can include frozen samples collected for other purposes. Samples can be associated with relevant information, such as age, gender, and clinical symptoms present in the subject; source of the sample; and methods of collection and storage of the sample.

The biological sample can be obtained from a subject using any means known in the art. For example, the sample can be obtained from the subject by removing the sample (e.g., a tumor tissue sample) from the subject, e.g., via a surgical procedure, a biopsy procedure, or by needle aspiration.

A biopsy comprises the process of removing a tissue sample for diagnostic or prognostic evaluation, and to the tissue specimen itself. Any biopsy technique known in the art can be applied to the methods described herein. The biopsy technique applied can depend on the tissue type to be evaluated (e.g., brain, colon, prostate, kidney, bladder, lymph node, liver, bone marrow, blood cell, lung, breast, etc.), the size and type of the tumor (e.g., solid or suspended, blood or ascites), among other factors. Representative biopsy techniques include, but are not limited to, excisional biopsy, incisional biopsy, needle biopsy, surgical biopsy, and bone marrow biopsy. An "excisional biopsy" refers to the removal of an entire tumor mass with a small margin of normal tissue surrounding it. An "incisional biopsy" refers to the removal of a wedge of tissue that includes a cross-sectional diameter of the tumor. Biopsy techniques are discussed, for example, in Harrison's Principles of Internal Medicine, Kasper, et al., eds., 16th ed., 2005, Chapter 70, and throughout Part V.

The measured or determined levels of proteolytically cleaved extracellular fragments of an Ig superfamily cell adhesion molecule in a biological sample derived from a subject, measured by the assay methods described herein, can be used for identifying a subject as having cancer associated with poor prognosis, monitoring the progress of cancer development in a subject, assessing the efficacy of a treatment for the cancer in a subject, identifying patients suitable for a particular treatment, predicting cancer relapse in a subject, and/or adjustment treatment of the cancer based on disease development, prognosis results, and/or efficacy of current treatment.

The measured or determined level of the proteolytically cleaved extracellular fragments of an Ig superfamily cell adhesion molecule may be relatively (i) higher, increased or greater; or (ii) lower, decreased or reduced when compared to level in a control or reference sample, or to a threshold level. In one embodiment, a determined or measured level may be classified as higher increased or greater if it exceeds a mean and/or median expression level of a reference population. In another embodiment, a measured or determined level may be classified as lower, decreased or reduced if it is less than the mean and/or median expression level of the reference population. In this regard, a reference population may be a group of subjects who have the same cancer type, subgroup, stage and/or grade as the subject for which the level is determined.

By comparing the level of a biomarker in a sample obtained from a subject to the reference value as described herein, it can be determined as to whether the subject has or is at risk for a target cancer associated with poor prognosis.

For example, if the level of the proteolytically cleaved extracellular fragments of an Ig superfamily cell adhesion molecule in a sample of the subject decreased as compared to the reference value, the candidate subject might be identified as having or at risk for the target cancer associated with poor prognosis.

Terms such as "higher", "increased" and "greater" as used herein refer to an elevated amount or level of the proteolytically cleaved extracellular fragments of an Ig superfamily cell adhesion molecule in the biological sample when compared to a control or reference level or amount. The expression level of the proteolytically cleaved extracellular fragments of an Ig superfamily cell adhesion molecule may be relative or absolute. In some embodiments, the level of proteolytically cleaved extracellular fragments of an Ig superfamily cell adhesion molecule is higher, increased or greater if its level is more than about 0.5%, 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 100%, 150%, 200%, 300%, 400% or at least about 500% above the level of proteolytically cleaved extracellular fragments of an Ig superfamily cell adhesion molecule of the respective or corresponding extracellular fragments in a control or reference level or amount.

The terms, "lower", "reduced" and "decreased", as used herein refer to a lower amount or level of the proteolytically cleaved extracellular fragments of an Ig superfamily cell adhesion molecule, when compared to a control or reference level or amount. The level of the proteolytically cleaved extracellular fragments of an Ig superfamily cell adhesion molecule may be relative or absolute. In some embodiments, the level of the proteolytically cleaved extracellular fragments of an Ig superfamily cell adhesion molecule is lower, reduced or decreased if its level of expression is less than about 95%, 90%, 80%, 70%, 60%, 50%, 40%, 30%, 20% or 10%, or even less than about 5%, 4%, 3%, 2%, 1%, 0.5%, 0.1%, 0.01%, 0.001% or 0.0001% of the level or amount of the proteolytically cleaved extracellular fragments of an Ig superfamily cell adhesion molecule of the respective or corresponding extracellular fragment in a control or reference level or amount.

The term "control sample" typically refers to a biological sample, such as sample, from a (healthy) non-diseased individual not having cancer. In one embodiment, the control sample may be from a subject known to be free of cancer or a sample that was obtained from the subject at an earlier timepoint. Alternatively, the control sample may be from a subject in remission from cancer. The control sample may be a pooled, average or an individual sample. An internal control is a marker from the same biological sample being tested.

As used herein, a determined or measured level of the proteolytically cleaved extracellular fragments of an Ig superfamily cell adhesion molecule in the biological may be an absolute or relative amount thereof. In further embodiments, the level of the proteolytically cleaved extracellular fragments of an Ig superfamily cell adhesion molecule is compared to a threshold level. A threshold level is generally a quantified level of the proteolytically cleaved extracellular fragments of an Ig superfamily cell adhesion molecule. Typically, a level of the proteolytically cleaved extracellular fragments of an Ig superfamily cell adhesion molecule in a biological sample that exceeds or falls below the threshold level is predictive of a particular disease state or outcome. The nature and numerical value (if any) of the threshold level will typically vary based on the method chosen to determine the level used in determining, for example, a prognosis and/or a response to anticancer therapy, in the subject.

A person of skill in the art would be capable of determining a threshold level of the proteolytically cleaved extracellular fragments of an Ig superfamily cell adhesion molecule in a biological sample that may be used in determining, for example, a prognosis and/or a response to anticancer therapy, using any method of measuring the level of the proteolytically cleaved extracellular fragments of an Ig superfamily cell adhesion molecule, such as those described herein. In one embodiment, the threshold level is a mean and/or median level (median or absolute) of the proteolytically cleaved extracellular fragments of an Ig superfamily cell adhesion molecule, that, for example, have the same cancer type, subgroup, stage and/or grade as said subject for which the level is determined. Additionally, the concept of a threshold level of should not be limited to a single value or result. In this regard, a threshold level may encompass multiple threshold levels that could signify, for example, a high, medium, or low probability of, for example, metastasis of the subject's cancer.

In one embodiment, a higher level of the proteolytically cleaved extracellular fragments of an Ig superfamily cell adhesion molecule indicates or correlates with relatively increased responsiveness of the cancer to an anti-cancer treatment. In alternative embodiments, a lower level of the one or plurality of the proteolytically cleaved extracellular fragments of an Ig superfamily cell adhesion molecule indicates or correlates with relatively decreased responsiveness of the cancer to the anti-cancer treatment.

In another embodiment, a lower level of the proteolytically cleaved extracellular fragments of an Ig superfamily cell adhesion molecule indicates or correlates with relatively increased responsiveness of the cancer to an anti-cancer treatment. In alternative embodiments, a higher level of the one or plurality of the proteolytically cleaved extracellular fragments of an Ig superfamily cell adhesion molecule indicates or correlates with relatively decreased responsiveness of the cancer to the anti-cancer treatment.

By way of example, the level of proteolytically cleaved extracellular fragments of PTPµ in human glioma tissue obtained from a subject was measured using an SBK4 peptide (SEQ ID NO: 7) conjugated to Texas Red, SBK4-TR, and found to correlate with pathologic features, including survival outcomes. The findings described in the Example indicate that high PTPµ biomarker levels are predictive of longer survival time for all glioma subtypes. Even when adjusted for age, sex, and IDH1 mutation status, high PTPµ biomarker levels correlate with increased survival in GBM patients.

It will be appreciated, that the method can further include determining the presence or level of at least one additional biomarker that indicates or correlates with at least one of prognosis for the cancer, the subject's survival, or responsiveness of the cancer to anti-cancer treatment. The additional biomarker can include, for example, gene, gene products, nucleic acids and/or proteins indicative of cancer prognosis.

Gene and/or gene products that can potentially be correlated with or indicative of cancer prognosis include ABCB1, ABCG2, ABI1, ABL1, ABL2, ACKR3, ACSL3, ACSL6, ACVR1B, ACVR2A, AFF1, AFF3, AFF4, AKAP9, AKT1, AKT2, AKT3, ALDH1A1, ALDH2, ALK, AMER1, ANGPT1, ANGPT2, ANKRD23, APC, AR, ARAF, AREG, ARFRP1, ARHGAP26, ARHGEF12, ARID1A, ARID1B, ARID2, ARNT, ASPSCR1, ASXL1, ATF1, ATIC, ATM, ATP1A1, ATP2B3, ATR, ATRX, AURKA, AURKB, AXIN1, AXL, BAP1, BARD1, BBC3, BCL10, BCL11A, BCL11B, BCL2, BCL2L1, BCL2L11, BCL2L2, BCL3, BCL6, BCL7A, BCL9, BCOR, BCORL1, BCR, BIRC3, BLM, BMPR1A, BRAF, BRCA1, BRCA2, BRD3, BRD4, BRINP3, BRIP1, BTG1, BTG2, BTK, BUB1B, C11orf30, C15orf65, C2orf44, CA6, CACNA1D, CALR, CAMTA1, CANT1, CARD11, CARS, CASC5, CASP8, CBFA2T3, CBFB, CBL, CBLB, CBLC, CCDC6, CCNB1IP1, CCND1, CCND2, CCND3, CCNE1, CD19, CD22, CD274, CD38, CD4, CD70, CD74, CD79A, CD79B, CD83, CDC73, CDH1, CDH11, CDK12, CDK4, CDK6, CDK7, CDK8, CDK9, CDKN1A, CDKN1B, CDKN2A, CDKN2B, CDKN2C, CDX2, CEBPA, CHCHD7, CHD2, CHD4, CHEK1, CHEK2, CHIC2, CHN1, CHORDC1, CIC, CIITA, CLP1, CLTC, CLTCL1, CNBP, CNOT3, CNTN1, CNTRL, COL1A1, COPB1, COX6C, CRBN, CREB1, CREB3L1, CREB3L2, CREBBP, CRKL, CRLF2, CRTC1, CRTC3, CSF1R, CSF3R, CTCF, CTLA4, CTNNA1, CTNNB1, CUL3, CXCR4, CYLD, CYP17A1, CYP2D6, DAXX, DDB2, DDIT3, DDR1, DDR2, DDX10, DDX3X, DDX5, DDX6, DEK, DICER1, DIS3, DLL4, DNM2, DNMT1, DNMT3A, DOT1L, DPYD, DUSP4, DUSP6, EBF1, ECT2L, EDNRB, EED, EGFR, EIF4A2, ELF4, ELK4, ELL, ELN, EML4, EP300, EPHA3, EPHA5, EPHA7, EPHA8, EPHB1, EPHB2, EPHB4, EPS15, ERBB2, ERBB3, ERBB4, ERC1, ERCC1, ERCC2, ERCC3, ERCC4, ERCC5, EREG, ERG, ERN1, ERRFI1, ESR1, ETV1, ETV4, ETV5, ETV6, EWSR1, EXT1, EXT2, EZH2, EZR, FAF1, FAIM3, FAM46C, FANCA, FANCC, FANCD2, FANCE, FANCF, FANCG, FANCL, FAS, FAT1, FBXO11, FBXW7, FCRL4, FEV, FGF10, FGF14, FGF19, FGF2, FGF23, FGF3, FGF4, FGF6, FGFR1, FGFR1OP, FGFR2, FGFR3, FGFR4, FH, FHIT, FIP1L1, FKBP1A, FLCN, FLI1, FLT1, FLT3, FLT4, FNBP1, FOXA1, FOXL2, FOXO1, FOXO3, FOXO4, FOXP1, FRS2, FSTL3, FUBP1, FUS, GABRA6, GAS7, GATA1, GATA2, GATA3, GATA4, GATA6, GID4, GLI1, GMPS, GNA11, GNA12, GNA13, GNAQ, GNAS, GNRH1, GOLGA5, GOPC, GPC3, GPHN, GPR124, GRIN2A, GRM3, GSK3B, GUCY2C, H3F3A, H3F3B, HCK, HDAC1, HERPUD1, HEY1, HGF, HIP1, HIST1H1E, HIST1H3B, HIST1H4I, HLF, HMGA1, HMGA2, HMGN2P46, HNF1A, HNMT, HNRNPA2B1, HNRNPK, HOOKS, HOXA11, HOXA13, HOXA9, HOXC11, HOXC13, HOXD11, HOXD13, HRAS, HSD3B1, HSP90AA1, HSP90AB1, IAPP, ID3, IDH1, IDH2, IGF1R, IGF2, IKBKE, IKZF1, IL2, IL21R, IL3RA, IL6, IL6ST, IL7R, INHBA, INPP4B, IRF2, IRF4, IRS2, ITGAV, ITGB1, ITK, ITPKB, JAK1, JAK2, JAK3, JAZF1, JUN, KAT6A, KAT6B, KCNJ5, KDM1A, KDM5A, KDM5C, KDM6A, KDR, KDSR, KEAP1, KEL, KIAA1549, KIF5B, KIR3DL1, KIT, KLF4, KLHL6, KLK2, KMT2A, KMT2C, KMT2D, KRAS, KTN1, L1CAM, LASP1, LCK, LCP1, LGALS3, LGR5, LHFP, LIFR, LMO1, LMO2, LOXL2, LPP, LRIG3, LRP1B, LUC7L2, LYL1, LYN, LZTR1, MAF, MAFB, MAGED1, MAGI2, MALT1, MAML2, MAP2K1, MAP2K2, MAP2K4, MAP3K1, MAPK1, MAPK11, MAX, MCL1, MDM2, MDM4, MDS2, MECOM, MED12, MEF2B, MEN1, MET, MITF, MKI67, MKL1, MLF1, MLH1, MLLT1, MLLT10, MLLT11, MLLT3, MLLT4, MLLT6, MMP9, MN1, MNX1, MPL, MRE11A, MS4A1, MSH2, MSH6, MSI2, MSN, MST1R, MTCP1, MTF2, MTOR, MUC1, MUC16, MUTYH, MYB, MYC, MYCL, MYCN, MYD88, MYH11, MYH9, NACA, NAE1, NBN, NCAM1, NCKIPSD, NCOA1, NCOA2, NCOA4, NDRG1, NF1, NF2, NFE2L2, NFIB, NFKB2, NFKBIA, NIN, NKX2-1, NONO, NOTCH1, NOTCH2, NOTCH3, NPM1, NR4A3, NRAS, NSD1, NT5C2, NTRK1, NTRK2, NTRK3, NUMA1, NUP214, NUP93, NUP98, NUTM1, NUTM2B, OLIG2, OMD, P2RY8, PAFAH1B2, PAK3, PALB2, PARK2, PARP1, PATZ1, PAX3, PAX5, PAX7, PAX8, PBRM1, PBX1, PCM1, PCSK7, PDCD1, PDCD1LG2, PDE4DIP, PDGFB, PDGFRA, PDGFRB, PDK1, PECAM1, PERI, PHF6, PHOX2B, PICALM, PIK3C2B, PIK3CA, PIK3CB, PIK3CD, PIK3CG, PIK3R1, PIK3R2, PIM1, PLAG1, PLCG2, PML, PMS1, PMS2, POLD1, POLE, POT1, POU2AF1, POU5F1, PPARG, PPP2R1A, PRCC, PRDM1, PRDM16, PREX2, PRF1, PRKAR1A, PRKCI, PRKDC, PRLR, PRPF40B, PRRT2, PRRX1, PRSS8, PSIP1, PSMD4, PTBP1, PTCH1, PTEN, PTK2, PTPN11, PTPRC, PTPRD, PTPRM, QKI, RABEP1, RAC1, RAD21, RAD50, RAD51, RAD51B, RAD51C, RAD51D, RAF1, RALGDS, RANBP17, RANBP2, RAP1GDS1, RARA, R131, RBM10, RBM15, RCOR1, RECQL4, REL, RELN, RET, RHOA, RHOH, RICTOR, RIPK1, RMI2, RNF213, RNF43, ROS1, RPL10, RPL22, RPL5, RPN1, RPS6KB1, RPTOR, RUNX1, RUNX1T1, S1PR2, SAMHD1, SBDS, SDC4, SDHA, SDHAF2, SDHB, SDHC, SDHD, SEPT5, SEPT6, SEPT9, SET, SETBP1, SETD2, SF1, SF3A1, SF3B1, SF3B2, SFPQ, SGK1, SH2B3, SH3GL1, SLAMF7, SLC34A2, SLC45A3, SLIT2, SMAD2, SMAD3, SMAD4, SMARCA4, SMARCB1, SMARCE1, SMC1A, SMC3, SMO, SNCAIP, SNX29, SOCS1, SOX10, SOX11, SOX2, SOX9, SPECC1, SPEN, SPOP, SPTA1, SRC, SRGAP3, SRSF2, SRSF3, SS18, SS18L1, SSX1, STAG2, STAT5, STAT4, STAT5B, STEAP1, STIL, STK11, SUFU, SUZ12, SYK, TAF1, TAF15, TAL1, TAL2, TBL1XR1, TBX3, TCEA1, TCF12, TCF3, TCF7L2, TCL1A, TEK, TERC, TERT, TET1, TET2, TFE3, TFEB, TFG, TFPT, TFRC, TGFB1, TGFBR2, THRAP3, TIMP1, TJP1, TLX1, TLX3, TM7SF2, TMPRSS2, TNFAIP3, TNFRSF14, TNFRSF17, TNFRSF18, TNFRSF9, TNFSF11, TOP1, TOP2A, TP53, TP63, TPBG, TPM3, TPM4, TPR, TRAF2, TRAF3, TRAF3IP3, TRAF7, TRIM26, TRIM27, TRIM33, TRIP11, TRRAP, TSC1, TSC2, TSHR, TTK, TTL, TYMS, U2AF1, U2AF2, UBA1, UBR5, USP6, VEGFA, VEGFB, VHL, VPS51, VTI1A, WAS, WEE1, WHSC1, WHSC1L1, WIF1, WISP3, WNT11, WNT2B, WNT3, WNT3A, WNT4, WNT5A, WNT6, WNT7B, WRN, WT1, WWTR1, XBP1, XPA, XPC, XPO1, YWHAE, YWHAZ, ZAK, ZBTB16, ZBTB2, ZMYM2, ZMYM3, ZNF217, ZNF331, ZNF384, ZNF521, ZNF703 and ZRSR2.

Determining, assessing, evaluating, assaying or measuring nucleic acids, such as RNA, mRNA and cDNA, of the cancer biomarker may be performed by any technique known in the art. These may be techniques that include nucleic acid sequence amplification, nucleic acid hybridization, nucleotide sequencing, mass spectroscopy and combinations of any these.

Determining, assessing, evaluating, assaying or measuring protein levels of the one or plurality protein biomarkers may be performed by any technique known in the art that is capable of detecting such proteins whether on the cell surface or internally expressed in the cancer cell. These techniques include antibody-based detection that uses one or more antibodies which bind the protein, electrophoresis, isoelectric focusing, protein sequencing, chromatographic techniques and mass spectroscopy and combinations of these, although without limitation thereto. Antibody-based detection may include flow cytometry using fluorescently-labeled antibodies, ELISA, immunoblotting, immunoprecipitation, radioimmunoassay (RIA) and immunocytochemistry, although without limitation thereto.

It will be appreciated that determining the expression of the one or plurality of biomarkers provided herein may include determining both the nucleic acid levels thereof, such as by nucleic acid amplification and/or nucleic acid hybridization, and the protein levels thereof. Accordingly, detection and/or measurement of expression of the one or plurality of markers from the cancer cells of the subject may be performed by any of those methods or combinations thereof described herein (e.g., measuring mRNA levels or an amplified cDNA copy thereof and/or by measuring a protein product thereof), albeit without limitation thereto.

In light of the foregoing, it will further be appreciated that an expression level of the one or plurality of markers provided herein may be an absolute or relative amount of an expressed gene or gene product thereof, inclusive of nucleic acids such as RNA, mRNA and cDNA, and/or protein.

By way of example, the prognosis of gliomas can be further determined using other known cancer biomarkers for gliomas. Such other known biomarkers can include, for example, upregulation of Epidermal Growth Factor Receptor (EGFR) expression, mutation in Tumor protein p53, mutation of an ATRX, mutation of IDH1/2, chromosome 7 (chr7) amplification coupled with a chromosome 10 (chr 10) deletion, cyclin-dependent kinase 4 (CDK4) amplification coupled with a cyclin dependent kinase inhibitor 2A (CDKN2A) deletion, chromosome 19 (chr19) amplification and a chromosome 20 (chr20) amplification, B-Raf gene (BRAF) mutation coupled with a Neurofibromin 1 (NF1) mutation.

Figure 7A:
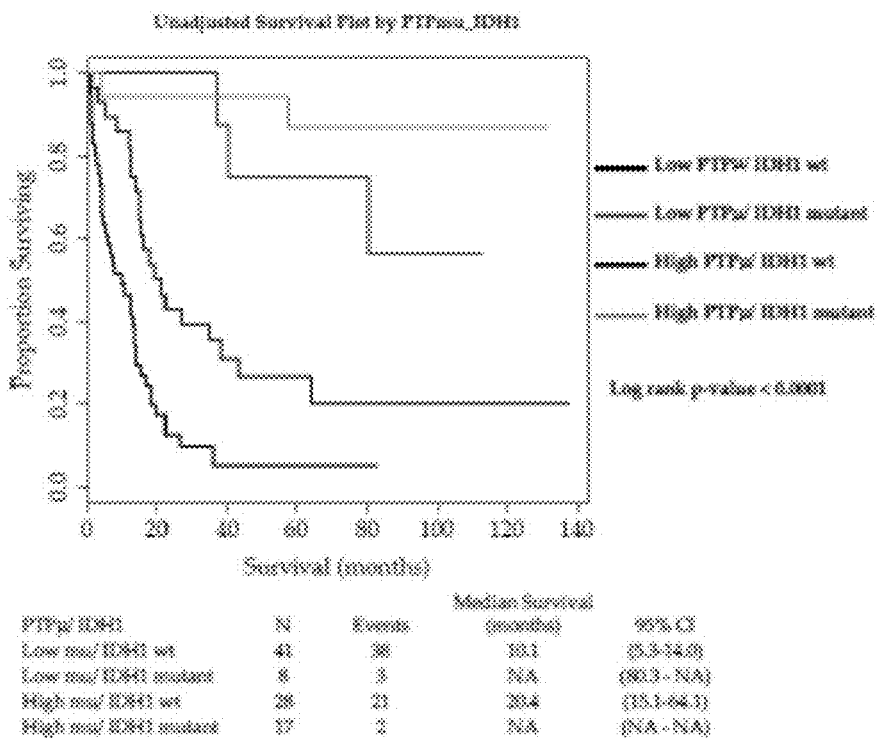
FIGS. 7 (A-B) illustrate Kaplan Meier survival plots for overall survival and recurrence-free survival by PTPμ low/IDH1 wild type (wt) versus PTPμ low/IDH1 mutant, PTPμ high/IDH1 wt, and PTPμ high/IDH1 mutant staining for patients with gliomas. (A) Unadjusted overall survival for lower grade (non-GBM) patients. (B) Overall survival adjusted for sex, age group for non-GBM patients.
Figure 7B:
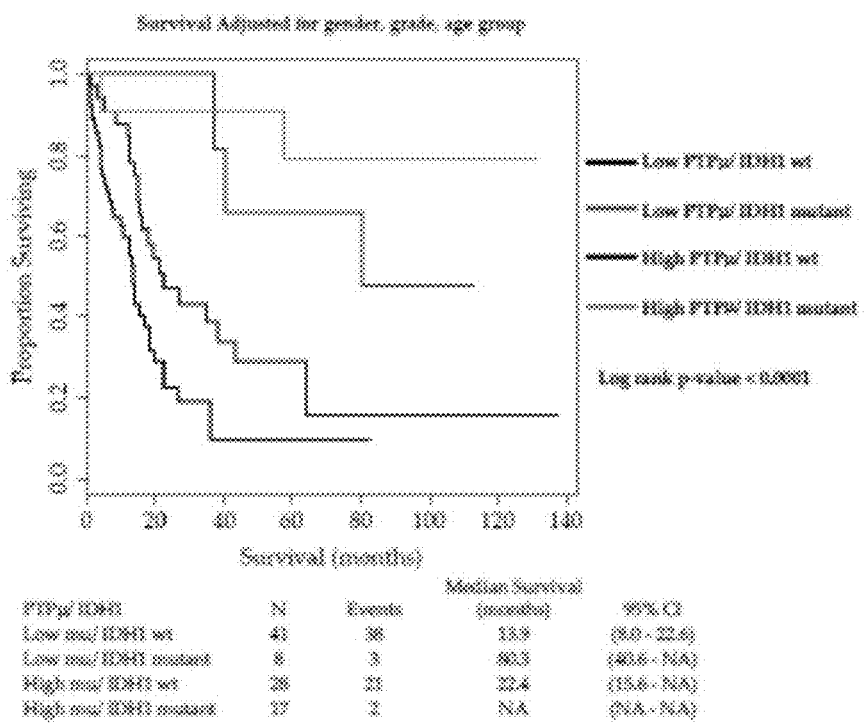

In one example, as shown in FIG. 7, brain tumor samples (glioma samples) obtained from subjects with brain tumors can be characterized as PTPµ low/IDH1 wild type (wt), PTPµ low/IDH1 mutant, PTPµ high/IDH1 wt, or PTPµ high/IDH1 mutant. As suggested by FIG. 7, patients having glioma samples with high levels of PTPµ staining and mutant IDH1 glioma had a significantly reduced hazard of death compared to patient having glioma samples with low levels of PTPµ and wild type IDH1 glioma patients.

It will further be appreciated that the methods described herein for predicting the responsiveness of a cancer to an anti-cancer agent may further include the step of administering to the subject a therapeutically effective amount of the anti-cancer treatment, such as an anticancer agent. In some embodiments, the anticancer treatment is administered when the level of the one or plurality of markers described herein indicates or correlates with relatively increased responsiveness of the cancer to the anti-cancer agent According to certain non-limiting embodiments, patients with the PTPµ low/IDH1 wt, PTPµ low/IDH1 mutant, or PTPµµ high/IDH1 wt glioma type may receive increased treatment as compared with patients with the PTPµ high/IDH1 mutant glioma type. According to certain non-limiting embodiments, patients with the PTPµ low/IDH1 wt, PTPµ low/IDH1 mutant, or PTPµ high/IDH1 wt glioma type may receive treatment appropriate for Grade 3 and Grade 4 gliomas.

According to certain non-limiting embodiments, patients with the PTPµ high/IDH1 mutant glioma type may receive treatment appropriate for Grade 1 or Grade 2 gliomas, with treatment appropriate for Grade 4 gliomas only if other factors so indicate.

The present disclosure further includes a kit for use in implementing any one or all of the above identifications. According to certain non-limiting embodiments, the kit can include reagents and other materials suitable for DNA and RNA analysis, including sequencing and, expression, mutation, or cluster analysis. According to certain non-limiting embodiments, the kit can include reagents and other materials suitable for protein extraction and analysis, including sequencing and identification of the quantity of protein. According to certain non-limiting embodiments, the kit can include reagents and other materials suitable for chromosome detection.

The present disclosure further includes a computer able to carry out the above methods to identify a glioma type using the above identifications. The computer can include a processor able to execute to identify a glioma type as well as a memory and an input module able to receive the identifications. According to certain non-limiting embodiments, the computer can receive the identifications as data from another computer via an input module. According to certain non-limiting embodiments, the computer can receive raw data and execute additional steps on the processor to create one or more identifications. The computer may further include an output to provide the glioma type and/or identifications to a user.

The following examples are included to demonstrate preferred embodiments.

Example 1

In this Example, we characterized the expression of PTPµ in human glioma tissue microarrays or in individual tumor samples using the SBK4 peptide conjugated to Texas Red, SBK4-TR, and correlated this with clinical and pathologic features, including survival outcomes. Our findings indicate that high PTPµ biomarker levels are predictive of longer survival time for all glioma subtypes. Even when adjusted for age, sex, and IDH1 mutation status, high PTPµ biomarker levels correlate with increased survival in GBM patients. These data provide an additional molecular diagnostic tool that can be predictive of survival for various gliomas, and support the use of the SBK agents for diagnosis, imaging, as well as fluorescence-guided surgery.

Materials and Methods

Study Ethics

Glioma patients were identified and prospectively consented to the Ohio Brain Tumor Study (PIs: Barnholtz-Sloan and Sloan) under approval from the University Hospitals Institutional Review Board. Clinical and pathological data was gathered for each patient and included age at diagnosis, sex, race, WHO grade, histological type, overall survival, overall vital status, recurrent status and recurrence free survival.

Reagents

The SBK4 peptide used for immunohistochemistry was synthesized as described. The N-terminal glycine of SBK4 peptide was coupled to Texas Red (TR; Molecular Probes Inc, Eugene Oreg.) as described to make the fluorescent agent. Anti-IDH1 R132H Monoclonal Antibody clone H09 (American Research Products [Dianova GmbH], Waltham, Mass.) reacts specifically with the isocitrate dehydrogenase 1 (IDH1) R132H point mutation in tissue sections from formalin-fixed brain tumor specimens.

Biomarker Labeling of Human Glioma Tissue

Patient tumor samples were obtained, formalin-fixed, and paraffin-embedded for analysis. Some samples were incorporated into tissue microarrays (TMAs) and some samples were placed on individual slides. Together, these TMAs and slides represented samples from 94 glioma patients (25 adolescent and young adult and 69 adult) with astrocytomas (n=12), oligodendroglioma (n=14), oligoastrocytoma (n=7), and GBM (n=61). Tissue staining with SBK4-TR has been described. Prior to staining, the TMAs or slides were deparaffinized and blocked with 2% goat serum in PBS for 20 minutes at room temperature (RT). The samples were then incubated with SBK4-TR agent diluted in 2% goat serum in PBS at RT for 1 hr in the dark. Following a PBS rinse, the TMAs or slides were coverslipped with Vectashield Hard Set Mounting Medium (Vector Laboratories, Inc., Burlingame, Calif.) and imaged on a Hamamatsu Nanozoomer S60 slide scanner (Bridgewater, N.J.). Some samples were also stained for the IDH1 mutation. For IDH-1 staining, antigen retrieval was performed in a citrate buffer. Antibody binding was detected using MACH4 horseradish peroxidase (Biocare, Pacheco, Calif.) and diaminobenzidine was used as chromogenic substrate. The sections were counterstained with hematoxylin and mounted with Ecomount (Biocare, Pacheco, Calif.) and imaged as above.

Tissue staining intensity for both PTPμ and IDH1 biomarkers was quantified by blinded observers. For PTPμ, a scoring system of 1-4 was used, where a staining level of 1 indicates the lowest staining and 4 indicates the highest staining levels. The staining was dichotomized as either low (score of 1 or 2) or high (score of 3 or 4). For IDH1, samples were scored as either positive for the mutation or negative as it is done clinically.

Statistical Analysis

Data were analyzed using version 3.5.1 of the R software. Summaries of PTPμ staining in comparison to the indicated clinicopathological characteristics were performed using the "tableone" package. Numbers and percentages of categorical variables were compared using the Chi square test. For continuous variables, means and standard deviations were calculated and compared using a t test. Survival analyses were performed using the "survival" and "survminer" packages in R. The Kaplan Meier method and log-rank test were used for generating unadjusted survival curves and testing for significance, as indicated. Multivariable models using Cox proportional hazards regression were generated to incorporate the possible contribution of additional clinicopathological features to overall survival. The final model selected for all patient data adjusts for sex, age group, tumor grade, and IDH1 mutation. The global log-rank p-values are shown for the survival curves with the three age groups indicated. In all cases, p-values <0.05 were considered statistically significant.

Results

Staining of Glioma Sections with the PTPμ biomarker

Human glioma tissue microarrays (TMAs) or individual glioma tumor samples were obtained from 94 patients including 25 adolescent and young adult (AYA) and 69 adults with astrocytomas (n=12), oligodendroglioma (n=14), oligoastrocytoma (n=7), and GBM (n =61). The clinicopathological characteristics of the patients combined with PTPμ biomarker staining results are summarized in Table 1. The 94 patients were fairly equally divided between those with PTPμ low (52%) and those with PTPμ high biomarker levels (48%; Table 1). Significantly more patients with PTPμ high were alive at the end of the follow-up period (22 patients) compared to those with PTPμ low biomarker levels (eight patients, p<0.002). These PTPμ high biomarker patients also had a significantly longer mean overall survival time of 48 months compared to the mean overall survival time of 22.4 months for the PTPμ low patients (p <0.001). Survival times shown in Table 1 represent mean survival times for all patients in a group, both for those where death was recorded and for those alive at the conclusion of the follow-up period. The mean time to recurrence shown in Table 1 for each group was calculated only from patients who experienced a recurrence.

The samples were stained for PTPμ with SBK4-TR, and a subset of those patient samples are shown in FIG. 1. Histology was visualized by staining with hematoxylin and eosin (H&E; FIG. 1A, D, F). The SBK4-TR staining was visualized with a fluorescent microscope. There was variable PTPμ staining of the tumor samples (FIG. 1C, E, F). The amount of fluorescence was divided into two categories, PTPμ low and PTPμ high, to reflect the biphasic nature of the results. As examples, A1 and A2 were classified as PTPμ low, while E7 and E8 illustrate PTPμ high expressing samples (FIG. 1C). The TMAs were also stained for mutant IDH1, as shown in FIG. 1b and f, and scored as positive or negative to replicate scoring by pathologists. A different TMA is shown in FIG. 1F with samples illustrating the range of PTPμ low and PTPμ high as well as wild-type and mutant IDH1 samples.

Analysis of Clinical Variables in Comparison to the PTPμ Biomarker

Figure 2B:
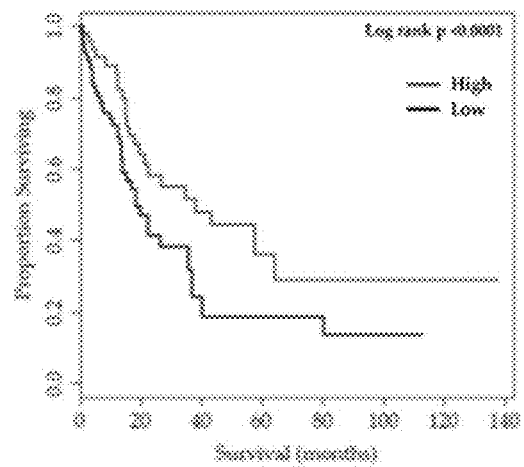

Kaplan Meier survival plots demonstrate that patients with PTPμ high biomarker staining have significantly increased survival relative to patients with PTPμ low biomarker staining. The last outcome recorded for a patient (i.e., living or deceased) at the end of the follow up period was carried forward to generate these survival plots. The survival of all glioma patients with PTPμ high and PTPμ low is plotted either unadjusted (FIG. 2A) or adjusted (FIG. 2B) by gender, grade, age group, and IDH1 mutation status. Median survival times are shown below each plot. As shown in FIG. 2A, the median survival of all glioma patients with PTPμ low was 13.3 months compared to 57.8 months for those with PTPμ high. After adjusting for sex, tumor grade, age group, and IDH1 mutation status, the median survival of all patients with PTPμ low was about half as long, 18.6 months, as those with PTPμ high staining, where the median survival was 38.2 months (FIG. 2B).

Figure 3:
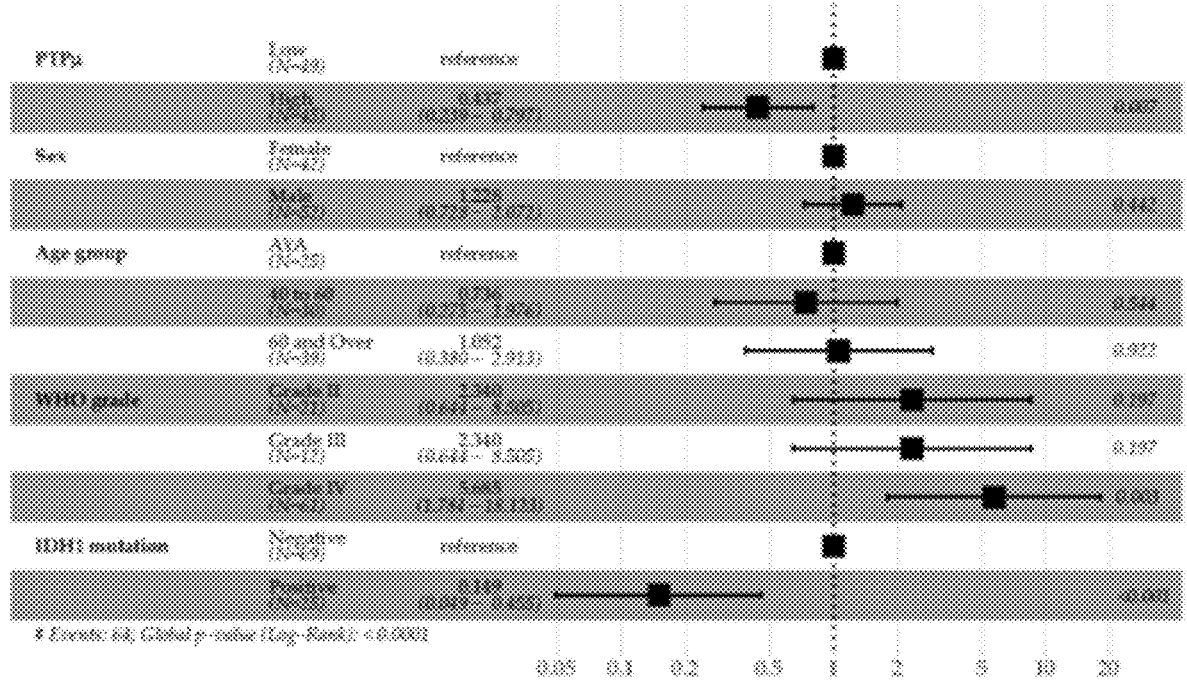
FIG. 3 illustrates a forest plot of Hazard Ratios (with 95% Confidence Intervals) from the final multivariable Cox proportional hazards regression model for overall survival for all glioma patients. Wald test p-values are shown.

Multivariable Cox proportional hazards regression survival models were generated to investigate the effects of PTPμ, sex, age, grade, IDH1 mutation status, and other parameters on overall survival. Results of the final model are summarized in the Forest Plot shown in FIG. 3. Sex, age, WHO tumor grade, and IDH1 mutation status were all included in the final model since all four characteristics are well validated prognostic factors in glioma as mentioned above. PTPμ high staining resulted in a significantly decreased hazard compared to PTPμ low staining (FIG. 3). Males showed a slightly increased hazard compared to females, but this difference was not significant. Similarly, there were no significant differences in the hazard of death among patients in the different age groups. Patients with grade IV tumors had significantly increased hazard ratios relative to patients with lower grade tumors. Consistent with previous studies, patients with mutant IDH1 had a significantly reduced hazard of death relative to wild-type IDH1 glioma patients (FIG. 3).

Figure 4A:
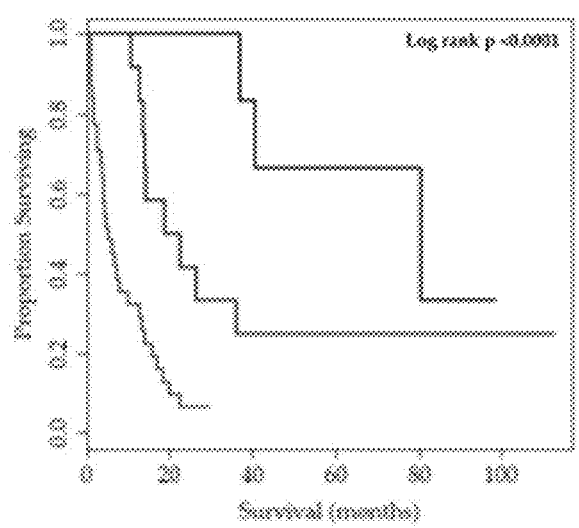
FIGS. 4(A-B) illustrate Kaplan Meier survival plots for overall survival by PTPμ low versus high staining and age at diagnosis for all glioma patients. (A) Unadjusted survival for PTPμ low patients. (B) Unadjusted survival for PTPμ high patients.
Figure 4B:
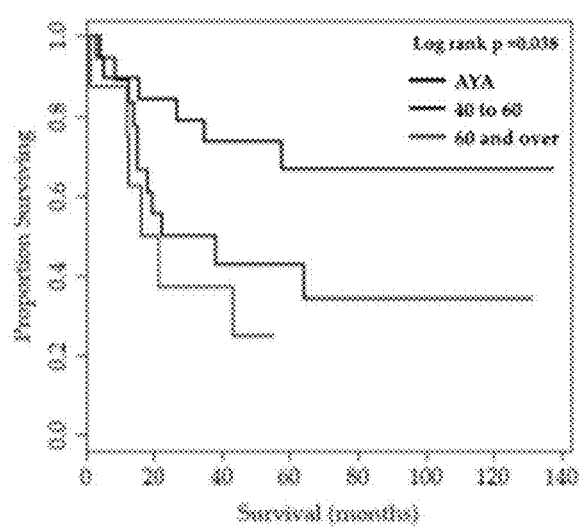

To better visualize overall survival among patients with PTPμ low and PTPμ high staining in different age categories, survival data for patients in each PTPμ category were plotted, as shown in FIG. 4. Unadjusted Kaplan Meier survival plots were calculated for glioma patients with PTPμ low (FIG. 4A) and PTPμ high (FIG. 4bB. Too few patients were available in each category to make meaningful Kaplan Meier survival plots that adjusted for sex, grade, and IDH1 mutation. Of the 49 patients with PTPμ low staining, six were AYA, 12 were patients aged 40 to 60, and 31 were patients aged 60 and over. In the PTPμ low group, younger patients had longer median survival times than older patients (FIG. 4A). Patients aged 60 and over with low levels of PTPμ staining had a median survival time of 5.3 months, patients 40-60 years old had a median survival of 20.6 months, and the AYA patients had an almost four-fold longer median survival of 80.3 months (FIG. 4A). The distribution of age groups was different for patients with PTPμ high staining; of the 45 high, 19 were AYA, 18 were aged 40 to 60, and only eight were aged 60 and over. As with PTPμ low biomarker staining, the unadjusted overall survival for patients in the 60 and over group was worse than that of the other two age categories for the PTPμ high biomarker (FIG. 4B). AYA patients with high levels of PTPμ had longer survival compared to the other the age groups (FIG. 4B), but median survival time could not be determined because only six deaths were recorded among the 19 AYA patients.

Comparison of PTPμ low and PTPμ high biomarker staining within a given age group reveals some interesting observations (FIG. 4). For instance, patients in the oldest age group with PTPμ high staining had a significantly longer median overall survival of 18.9 months (FIG. 4B) compared to 5.3 months for those patients 60 and over in the PTPμ low group (FIG. 4a; log rank p-value=0.025). The trend was similar although not statistically significant for the other two age groups. In the 40 to 60 age category, the median survival was 30.3 months for the PTPμ high versus 20.6 months for PTPμ low patients. The median survival time for AYA patients with PTPμ high could not be determined and cannot be compared to that of AYA patients with PTPμ low in this study due to the length of the follow-up period. Of note, 13 of 19 PTPμ high AYA patients survived through the follow-up period compared to three of six in the PTPμ low group.

Figure 5A:
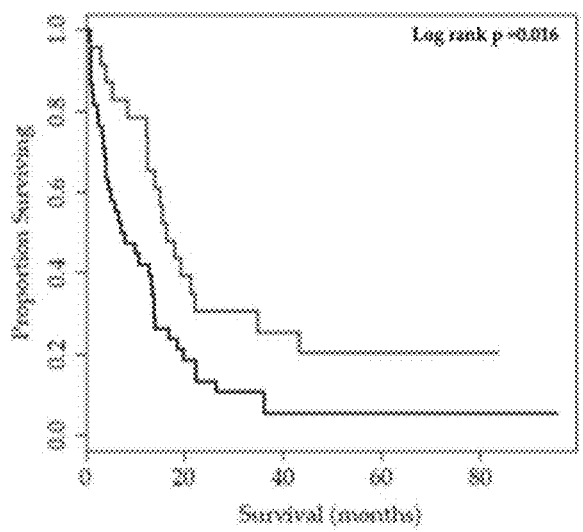
FIGS. 5(A-D) illustrate Kaplan Meier survival plots for overall survival and recurrence-free survival by PTPμ high versus PTPμ low staining for GBM patients only. (A) Unadjusted overall survival for GBM patients. (B) Overall survival adjusted for sex, age group, and IDH1 mutation for GBM patients. (C) Unadjusted recurrence-free survival for GBM patients. (D) Overall recurrence-free survival adjusted for sex, age group, and IDH1 mutation for GBM patients. Median overall survival or recurrence-free survival with 95% Confidence Intervals are shown below each plot. Based on log-rank test, recurrence-free survival curves were not significantly different between PTPμ high and low patients for either unadjusted or adjusted curves.
Figure 5B:
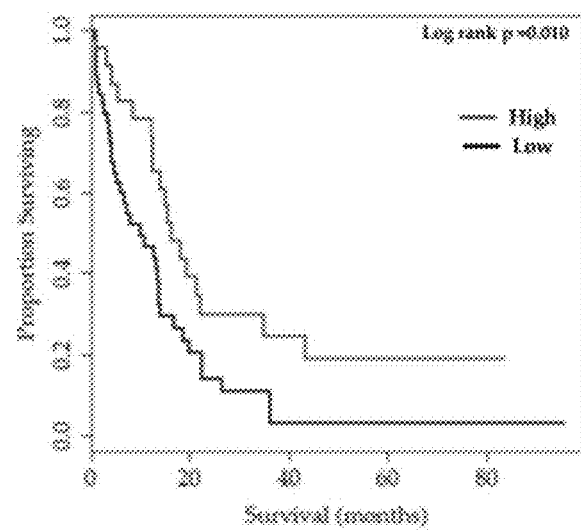
Figure 5C:
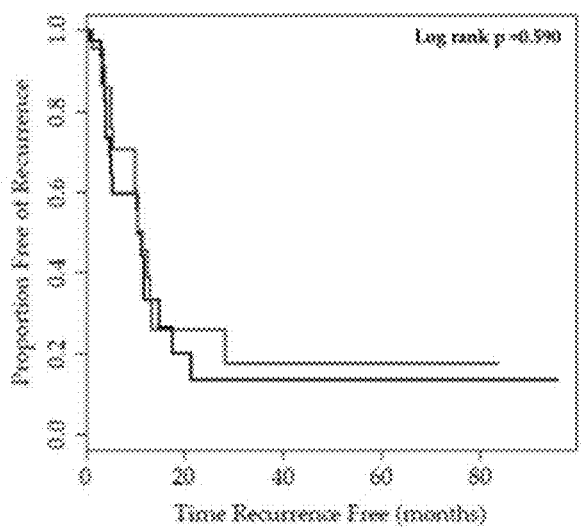
Figure 5D:
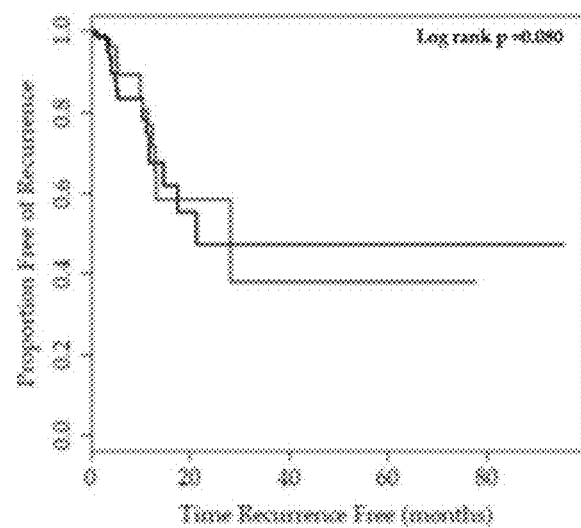

Next, the 61 patients with GBM were analyzed separately to better examine the relationship between survival and PTPμ staining in these patients. Kaplan Meier survival plots for overall survival are shown unadjusted or adjusted for sex, age group, and IDH1 mutation status (FIG. 5). GBM patients with PTPμ high staining showed significantly better survival compared to those with PTPμ low staining in both unadjusted (FIG. 5A) and adjusted plots (FIG. 5B). In contrast, no significant differences were detected between GBM patients with PTPμ low and PTPμ high staining in terms of recurrence-free survival (FIG. 5 C,D).

Figure 6A:
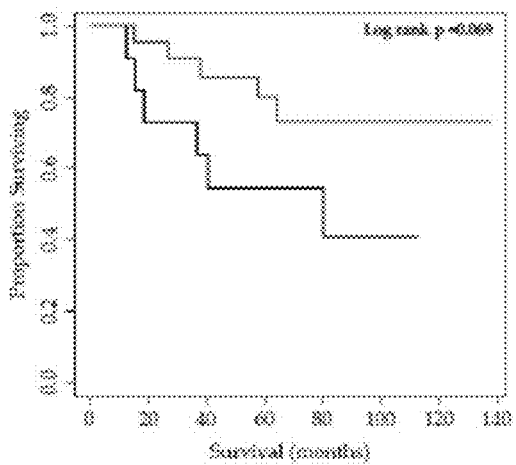
FIGS. 6(A-D) illustrate Kaplan Meier survival plots for overall survival and recurrence-free survival by PTPμ high versus PTPμ low staining for patients with lower grade gliomas. (A) Unadjusted overall survival for lower grade (non-GBM) patients. (B) Overall survival adjusted for sex, age group, and IDH1 mutation for non-GBM patients. (C) Unadjusted recurrence-free survival for non-GBM patients. (D) Overall recurrence-free survival adjusted for sex, age group, and IDH1 mutation for non-GBM patients. Median overall survival or recurrence-free survival with 95% CIs are shown below each plot. Based on the log-rank test, the adjusted recurrence-free survival curves were significantly different between PTPμ high and low non-GBM patients.
Figure 6B:
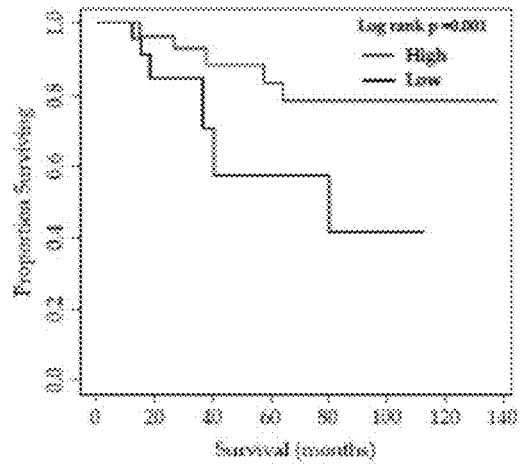
Figure 6C:
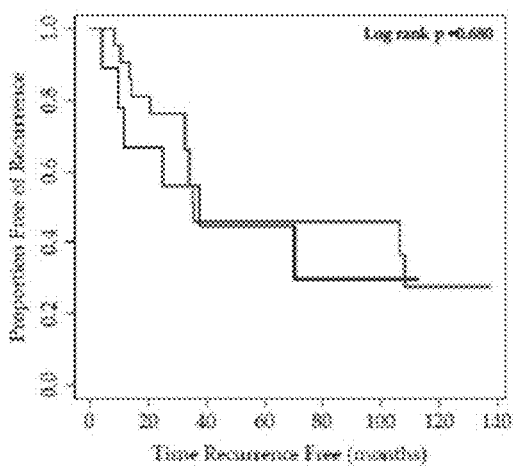
Figure 6D:
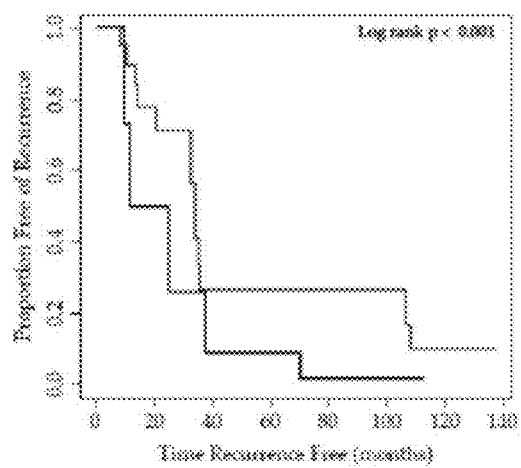

Finally, we examined the 33 remaining patients with lower grade gliomas (non-GBM), including astrocytomas (grade II and III), oligoastrocytomas, and oligodendrogliomas, to determine whether PTPμ staining correlated with overall survival (FIG. 6A,B) or recurrence-free survival (FIGS. 6C,D). As with GBM patients, patients with lower grade tumors but PTPμ high levels had longer overall survival than those with PTPμ low levels, although this difference was only significant after adjusting for sex, age group, and IDH1 mutation status (FIG. 6B). There was no difference in the unadjusted recurrence-free survival for glioma patients with non-GBM tumors with high and low PTPμ biomarker staining (FIG. 6C). However, after adjusting for sex, age group, and IDH1 mutation status, the PTPμ high non-GBM glioma patients had significantly longer recurrence free survival times than the PTPμ low non-GBM patients, 34.1 versus 11.8 months, respectively (FIG. 6D).

TABLE 1

Clinicopathological characteristics of glioma patients from the Ohio Brain Tumor Study with low and high staining for PTPμ.

| Variable | Category | PTPμ Low | PTPμ High | p test |
| --- | --- | --- | --- | --- |
| Number | | 49 | 45 | |
| Sex (%) | Female | 17 (34.7) | 25 (55.6) | 0.068 [1] |
| | Male | 32 (65.3) | 20 (44.4) | |
| Race (%) | Asian | 1 (2.0) | 0 (0.0) | 0.546 [1] |
| | Black | 2 (4.1) | 1 (2.2) | |
| | White | 46 (93.9) | 44 (97.8) | |
| Age at Diagnosis [mean (sd)] | | 62.2 (14.4) | 46.3 (15.5) | <0.001 [2] |
| Histologic Type (%) | Astrocytoma | 3 (6.1) | 9 (20.0) | 0.044 [1] |
| | Glioblastoma | 38 (77.6) | 23 (51.1) | |
| | Oligoastrocytoma | 2 (4.1) | 5 (11.1) | |
| | Oligodendroglioma | 6 (12.2) | 8 (17.8) | |
| WHO Grade (%) | Grade II | 5 (10.2) | 16 (35.6) | 0.010 [1] |
| | Grade III | 6 (12.2) | 6 (13.3) | |
| | Grade IV | 38 (77.6) | 23 (51.1) | |
| Recurrence Status (%) | No | 22 (47.8) | 16 (36.4) | 0.375 [1] |
| | Yes | 24 (52.2) | 28 (63.6) | |
| Recurrence time in months [mean (sd)] | | 12.8 (14.9) | 22.6 (26.4) | 0.114 [2] |
| Survival Status (%) | Alive | 8 (16.3) | 22 (48.9) | 0.002 [1] |
| | Deceased | 41 (83.7) | 23 (51.1) | |
| Survival time in months [mean (sd)] | | 22.4 (27.9) | 48.0 (38.1) | <0.001 [2] |
| Age Group (%) | AYA | 6 (12.2) | 19 (42.2) | <0.001 [1] |
| | 40 to 60 | 12 (24.5) | 18 (40.0) | |
| | 60 and Over | 31 (63.3) | 8 (17.8) | |
| IDH1 mutation (%) | Negative | 41 (83.7) | 28 (62.2) | 0.034 [1] |
| | Positive | 8 (16.3) | 17 (37.8) | |

[1] p-value from Chi-Square test
[2] p-value from t test
[3] Adolescent and Young Adult The most recent WHO Classification of Tumors of the Central Nervous System recommendations combine basic histology with either immunohistochemical or genetic tests for mutated IDH1 status, transcriptional regulator (ATRX) loss, and TP53 mutation or 1p/19q chromosomal deletion status to differentiate tumors. Using these molecular markers, gliomas can be more accurately classified as diffuse astrocytoma, oligodendroglioma, oligoastrocytoma, or the glioma with the worst overall prognosis, GBM. Of particular interest was the recommendation that molecular data and genotype overrule histology when discordant results arise.

Sequencing studies by The Cancer Genome Atlas (TCGA) identified the common mutation of IDH1 in GBM, with an observation that ~10% of GBM patients harbored IDH1 mutations. IDH1 mutations were associated with increased overall survival of GBM patients and occurred preferentially in young patients and those with secondary GBM, that is GBM progressing from a lower grade glioma as opposed to GBMs that arise de novo, i.e., primary GBM. A further refinement of glioma subtypes was accepted in the 2016 WHO guidelines by adding ATRX and TP53 mutational analysis alongside evaluation of 1p/19q chromosomal co-deletion. GBMs and astrocytomas are classified as IDH mutant or wild-type. Oligodendrogliomas can be distinguished from astrocytomas based on ATRX and TP53 mutations (observed in astrocytomas only) versus 1p/19q co-deletion (observed in oligodendrogliomas only along with IDH1 mutation). The use of immunohistochemistry for both IDH1 and ATRX mutation analysis should simplify the adoption of molecular diagnostics in the neurohistological setting. Based on molecular findings, new predictions for disease outcome can also be determined. For example, the presence of IDH1 mutations and 1p/19q co-deletions are associated with better survival outcomes for grade II, III, and IV gliomas, which may be relevant for determining treatment options for lower grade glioma patients with worse prognoses.

The data presented here suggest that high levels of PTPμ staining correlate with longer overall survival (anywhere from one and a half to three times longer) for patients of similar age. Since high PTPμ staining is correlated with improved survival of all age groups, the PTPμ biomarker may be an important prognostic marker. Unlike the markers discussed above, the changes observed in PTPμ in glioma are all post-translational in nature and not at the level of DNA. There is little evidence of PTPμ changes at either the DNA or the RNA level in brain tumors in the literature. The TCGA database indicates 13 mutations in the PTPμ gene (PTPRM) coding region, most of them low impact mutations. We previously observed differences in full-length PTPμ and proteolytic fragments of PTPμ in different glioma types, including GBM by immunoblot. When full-length PTPμ protein was added back to the invasive glioma LN-229 cell line, a cell line characterized by low amounts of full length PTPμ and high amounts of PTPμ fragments, cell migration was reduced. We found that PTPμ fragment expression was essential for promoting cell migration and cell survival in this cell line. Based on these results, we hypothesized that proteolytic cleavage of PTPμ impacts adhesion between adjacent cells, leading to a loss of contact inhibition of growth and promotion of cancer cell migration and invasion.

PTPμ high biomarker staining and IDH1 mutation both substantially reduced the hazard ratio of death, as shown in FIG. 3. Additional studies with more patients in each age group are needed to determine whether these biomarkers are involved in one or more common pathways leading to oncogenesis and/or prolonged survival.

Current practice is to utilize Clinical Laboratory Improvements Amendments (CLIA)-approved and commercially available monoclonal antibodies (mAbs) for the most common mutation of IDH1 and ATRX for routine grading of gliomas. If validated by additional studies, the SBK4-TR agent could be used in a similar setting and would allow quick and convenient one-step staining, as the Texas Red fluorophore is already conjugated to the SBK4 peptide. In future studies, we will use this same reagent to validate our results in an independent dataset of patient tissue.

In addition to using the SBK agents to predict patient outcomes, these agents could also be used in fluorescence-guided surgical resection of glioma for patients whose biopsy is positive for the PTPμ biomarker. 5-ALA is currently approved to be used in GBM surgery as it distinguishes tumor tissue from normal tissue by the preferential conversion of 5-ALA to fluorescent porphyrins (PpIX) in the heme biosynthesis cycle, which occurs at a higher rate in epithelial and tumor tissue. PpIX fluoresces under 400-410 nm wavelength excitation and emits at 635-705 nm and can be visualized with a fluorescent surgical microscope. It is very effective at delineating the main GBM tissue mass, with 92% positive predictive value, 77% specificity, and 79% negative predictive value, and was recently approved by the U.S. FDA for this purpose. However, it is less effective at labeling the dispersive GBM tumor border. The use of 5-ALA in the surgical resection of GBM results in a significant improvement in the extent of tumor resection (65% versus 36% with white light alone) and yields an improvement in six month progression-free survival. From previous studies, we know that the SBK agents are very effective at labeling the main tumor mass and the tumor's invasive edge. The SBK agents can be conjugated to any fluorophore, including those in the near-infrared range to minimize tissue interference. Since the PTPμ biomarker signifies cancer and the data presented demonstrate that the SBK4-TR agent labels both low- and high-grade glioma tissue, SBK4-TR could be useful for fluorescence-guided surgical resection of gliomas, either alone or multiplexed with 5-ALA for double labeling.

Brain tumors are the third most common malignancy in AYA patients between 15 and 39 years old. Until recently, AYA populations have been lumped with either pediatric or adult patients, and their treatment has varied between following pediatric or adult guidelines, neither of which may be appropriate for this disease. With the advent of molecular characterization of malignancy, fundamental differences between AYA patients and other age groups have been identified, clarifying that separate disease mechanisms are at play. In the case of glioma, pediatric, AYA, and adult patients have molecular distinctions between and within different glioma grades. In GBM, for example, TP53 and IDH1 mutations and phosphatase and tensin homolog (PTEN) deletion are frequently observed in patients under 40, as is hypermethylation of the CpG island methylator (C-GIMP) phenotype. All are correlated with better prognosis. In this data set, there are higher levels of the PTPμ biomarker in AYA patients and in 40 to 60 adult glioma patients, while patients 60 years and over tend to have low PTPμ staining.

In older GBM patients, epidermal growth factor receptor (EGFR) amplification and PTEN deletions are observed in a majority of cases, and IDH1 mutations are rarely observed. Of note, our data included a subset of GBM patients over 60 with PTPμ high staining and median survival times more than three times that of GBM patients in the same age group with PTPμ low staining. As with the IDH1 mutation, PTPμ high staining correlates with improved survival. Unlike IDH1 mutation status, the PTPμ biomarker may be a relevant prognosis marker for all age groups. In summary, the data presented here indicate the exciting possibility that the staining of the PTPμ biomarker may be used to predict clinical outcomes of glioma patients.

Example 2

We tested the efficacy of the SBK4 agent conjugated to a fluorophore as a one-step molecular diagnostic in human glioma tissue and found it detected aggressive tumors, suggesting that adoption of the use of SBK4 in patient biopsy tissue could help stratify patient risk. Given these initial findings in glioblastoma, we evaluated the efficacy of the fluorescent SBK2 agent in other solid cancer types, including gynecologic cancers.

Materials and Methods

Study Ethics and Patient Information

Patients were identified and prospectively consented to the Study (PIs: Difeo and Avril) under approval from the University Hospitals Institutional Review Board. Clinical and pathological data were gathered for some patients and included age at diagnosis, sex, race, WHO grade, tumor stage, histological type, and overall survival. Normal tissue was acquired from patients undergoing surgical resection.

Reagents

The SBK4 peptide used for tissue staining was synthesized as described. The N-terminal glycine of SBK4 peptide was coupled to Texas Red (TR; Molecular Probes Inc, Eugene, Oreg., USA) as described to make the fluorescent agent. Anti-p53 Monoclonal or Ki-67 antibodies were used to counterstain tissue sections, to indicate nuclear staining of p53 typical in high-grade serous ovarian carcinoma.

Biomarker Labeling of Human Gynecologic Tissue

All samples used for this study were obtained from the Difeo and Avril labs. The Avril group generated tissue microarrays of several gynecologic cancers (TMAs) to facilitate screening a large number of patient biopsy tissues. The Difeo lab generated TMAs that included sections from patient derived xenografts (PDXs) matched to original patient tumor tissue sections. Additional individual biopsy and normal tissue samples were stained as individual slides. Together, these TMAs and slides represented samples from 73 patients (49 with gynecologic cancer, 22 sections from patients without cancer, and 2 patients with gynecologic cancer tissue and control tissue samples collected). The following gynecologic cancer types were represented in the dataset: endometrial clear cell carcinoma (n=3), endometrial endometrioid carcinoma (n=18), endometrial high-grade serous carcinoma (n =6), endometrial leiomyosarcoma (n=1), endometrial undifferentiated carcinoma (n=1), endometrial undifferentiated sarcoma (n=1), neuroendocrine tumor of the uterus (small cell) (n=1), ovarian carcinosarcoma (n=1), ovarian borderline serous (n=1), ovarian high-grade villoglandular carcinoma (n=1), ovarian high-grade serous carcinoma (n=16), ovarian endometrioid carcinoma (n=1).

Tissue staining with SBK4-TR was described. Positive controls (GBM) and negative controls (Epilepsy) were tested with the TMAs or individual slides. Tumor samples were obtained formalin-fixed and paraffin-embedded. Prior to staining, the TMAs or slides were deparaffinized and blocked with 2% goat serum in phosphate buffered saline (PBS) for 20 min at room temperature (RT). The samples were then incubated with SBK4-TR agent diluted in 2% goat serum in PBS at RT for 1 hr in the dark. Following a PBS rinse, the TMAs or slides were coverslipped with Vectashield Hard Set Mounting Medium (Vector Laboratories, Inc., Burlingame, Calif., USA) and imaged on a Hamamatsu Nanozoomer S60 slide scanner (Bridgewater, N.J., USA). Some samples were also stained for the IDH1 mutation. Tissue staining for both PTPµ was quantified using Image J.

Results

Gynecological Cancer Tissue Microarray Staining with the PTPµ Biomarker

Figure 8:
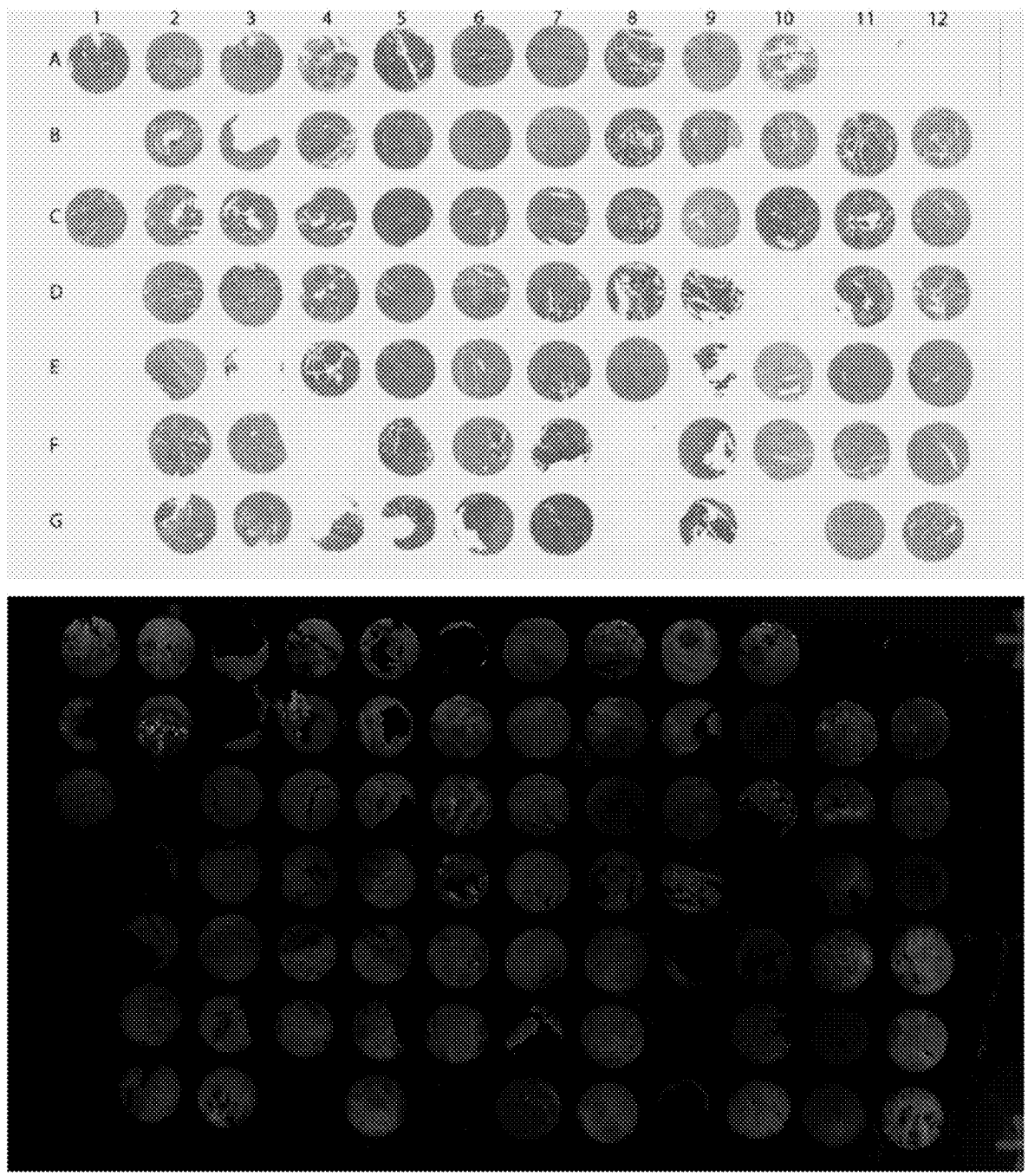
FIG. 8 illustrates a gynecological cancer tissue microarray (TMA) stained with SBK-4-TR.

Human gynecologic cancer tissue microarrays (TMAs) or individual normal and tumor samples were obtained from 73 patients including from 49 patients with cancer and 22 patients without cancer, and 2 patients with both control and cancer tissue samples collected. The staining observed with SBK4-TR varied amongst individual patients within the TMAs, as shown in FIG. 8.

Figure 9:
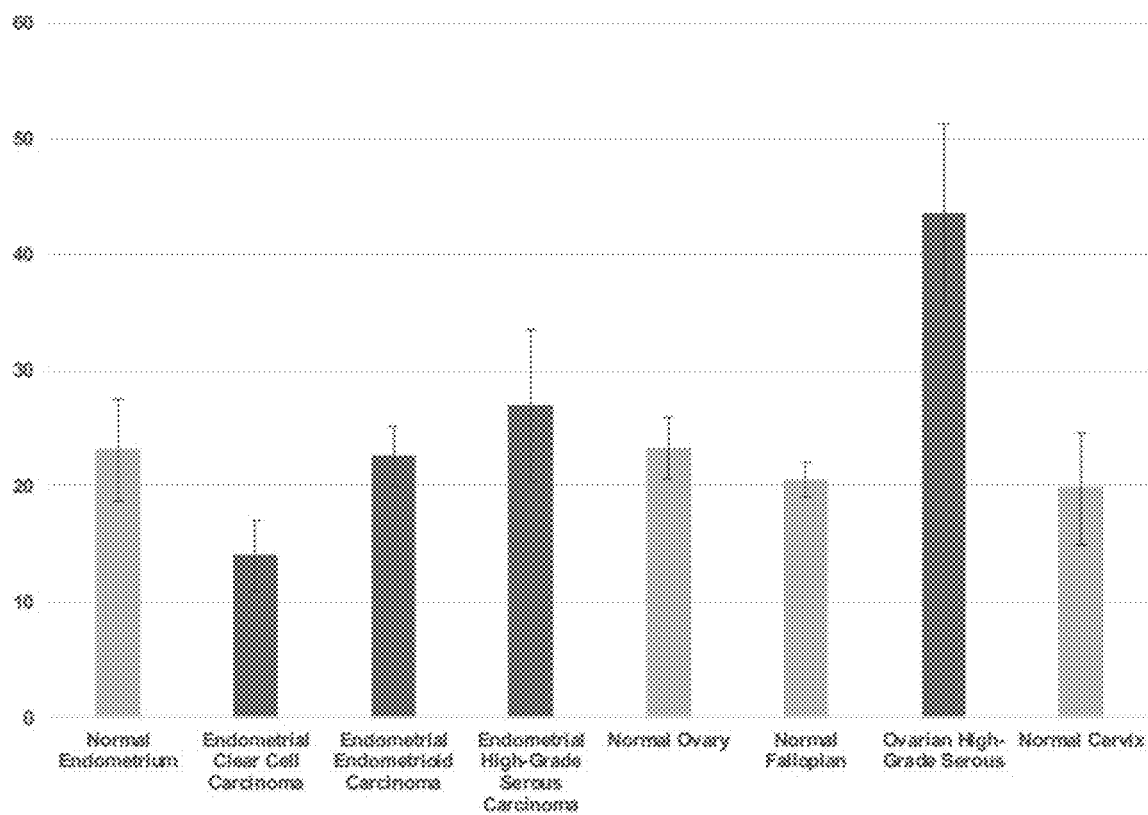
FIG. 9 illustrates a graph showing SBK-4 TR staining of normal tissue compared to cancer tissue from patients.

PTPµ Biomarker Staining Higher in Ovarian Serous Carcinoma Tumor than Normal Ovary We compared the average SBK4-TR labeling of tumor types that had three or more samples to normal tissue controls using the values generated with Image J analysis of the entire tissue sections (FIG. 9). We observed that SBK4-TR labeling was significantly higher for the high-grade serous ovarian carcinoma tissue compared to both normal ovary or normal fallopian tube (FIG. 9). For the other tumor tissue types, including endometrial endometrioid cancer, high-grade serous endometrial carcinoma or endometrial clear cell carcinoma we had small samples sizes. Those tissues did not have statistically significantly higher SBK4-TR staining than control tissue. However, the majority of cancer samples were higher than control normal tissue.

Figure 10:
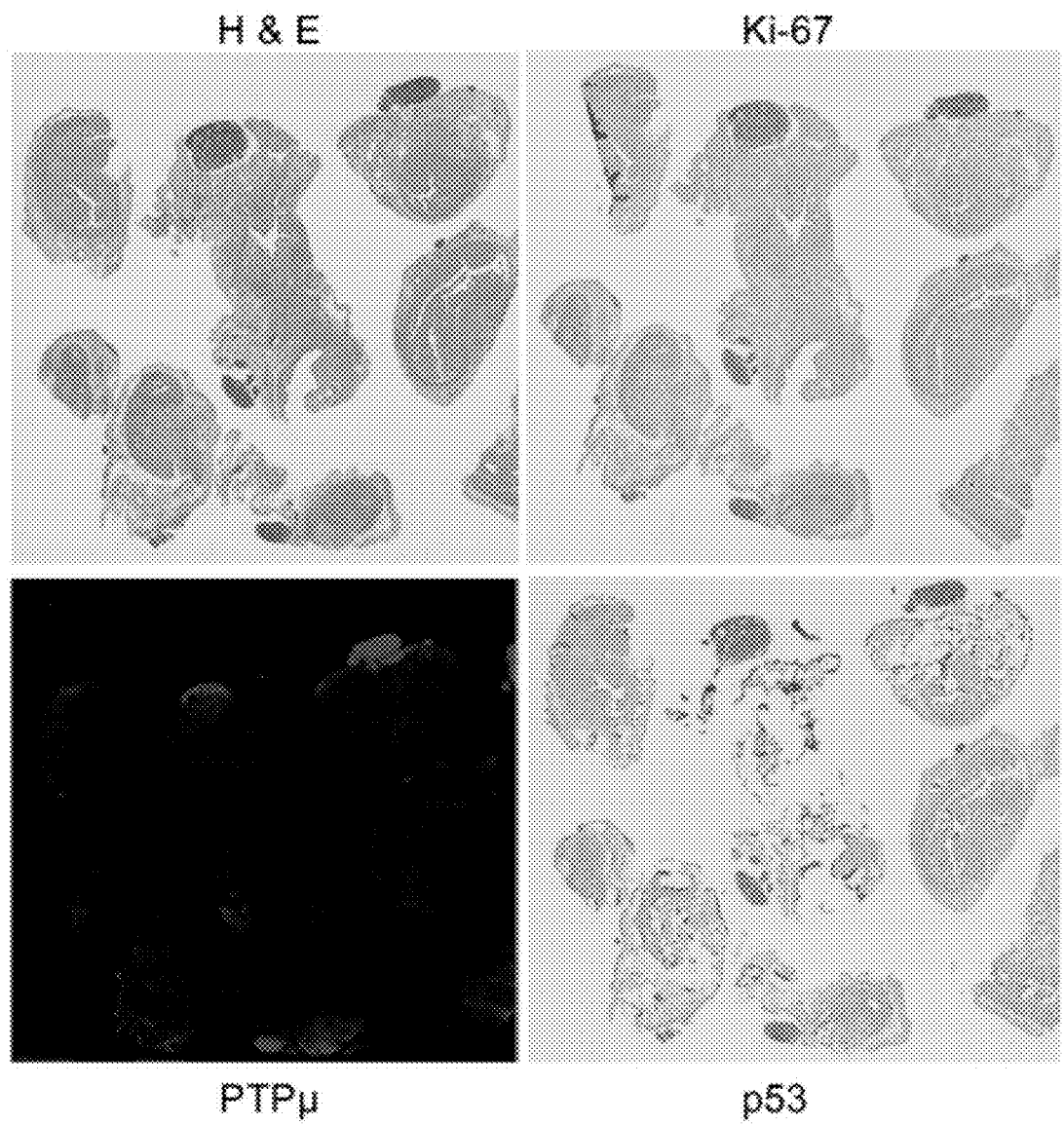
FIG. 10 illustrates SBK-4 TR labeling of tumors from patients and corresponding staining with p53 and Ki-67 staining.

Detailed evaluation of PTPµ biomarker expression in a patient with multiple lesions demonstrates that the sites of high SBK4-TR labeling correspond to areas of high p53 and Ki-67 staining (FIG. 10).

Figure 11:
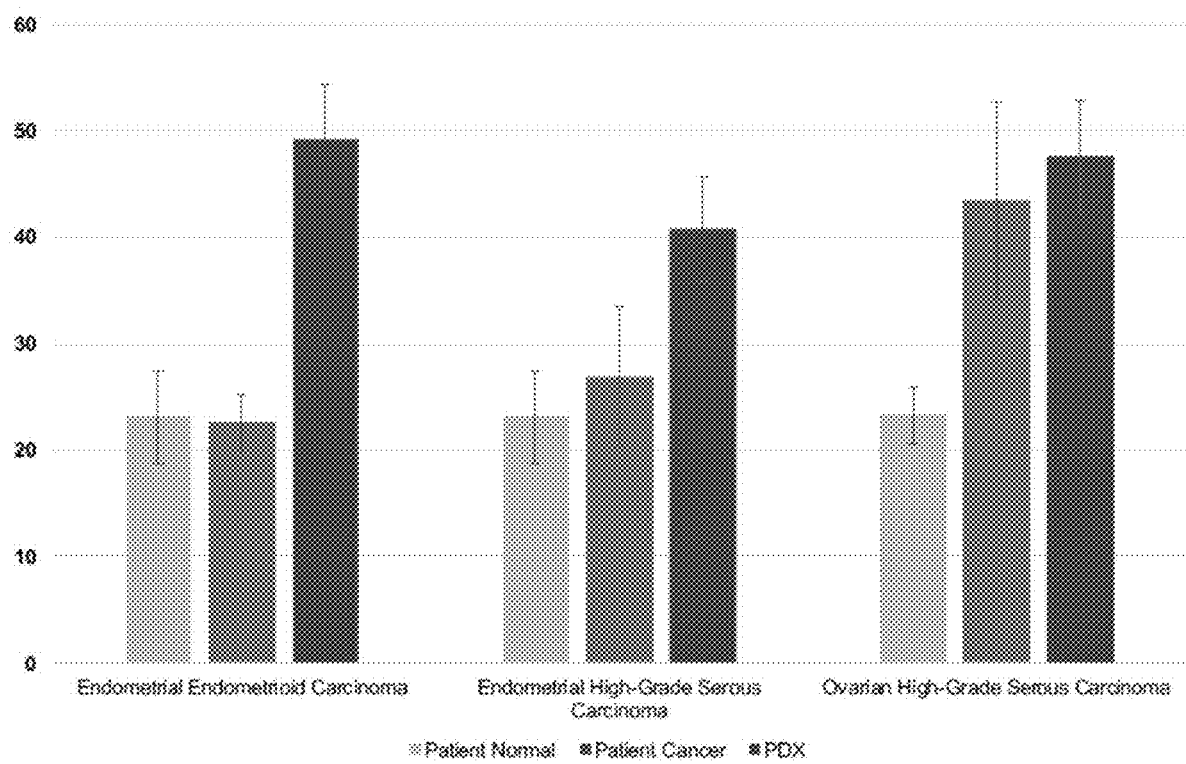
FIG. 11 illustrates a graph showing SBK-4 TR staining of normal tissue compared to cancer tissue from patients and patient derived xenograft (PDX) models.
Figure 12:
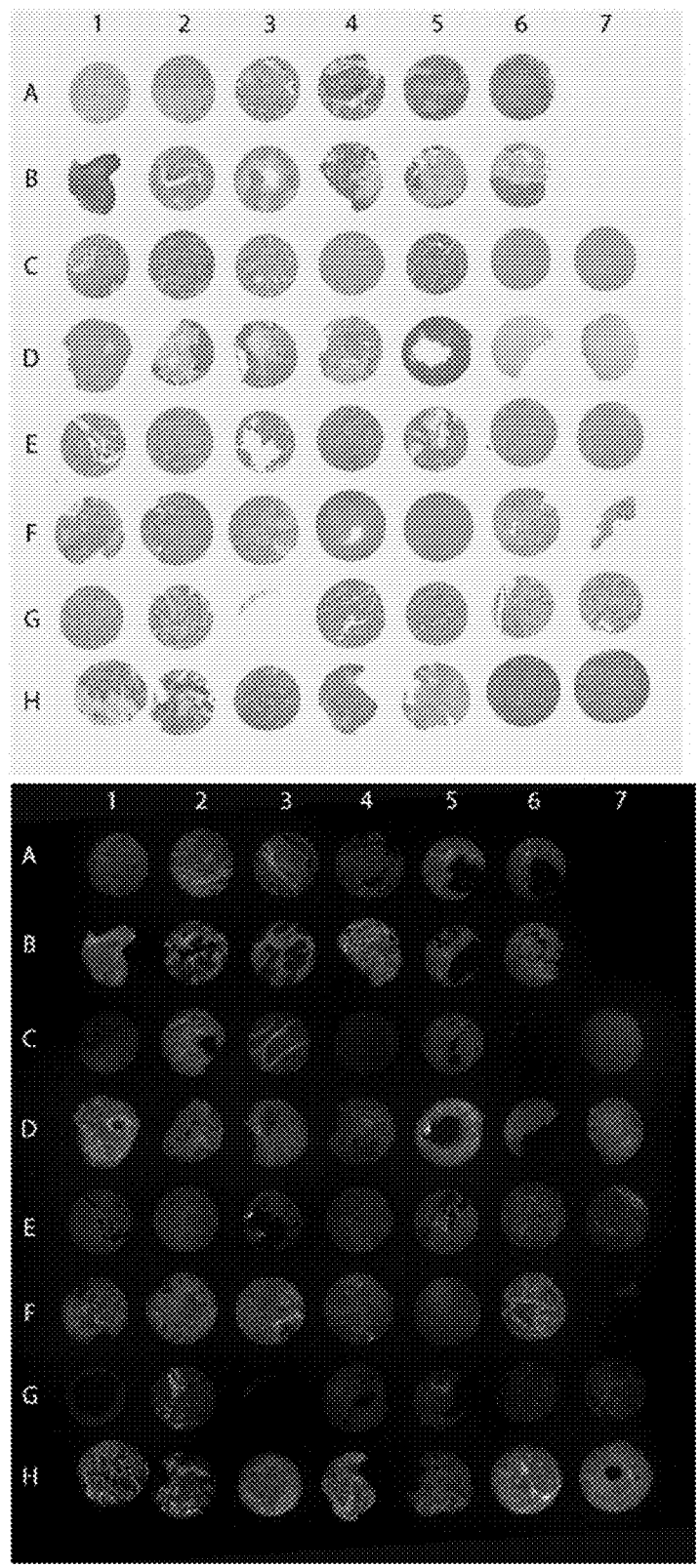
FIG. 12 illustrates PDX tissue microarray (TMA) stained with SBK-4 TR.
Figure 13:
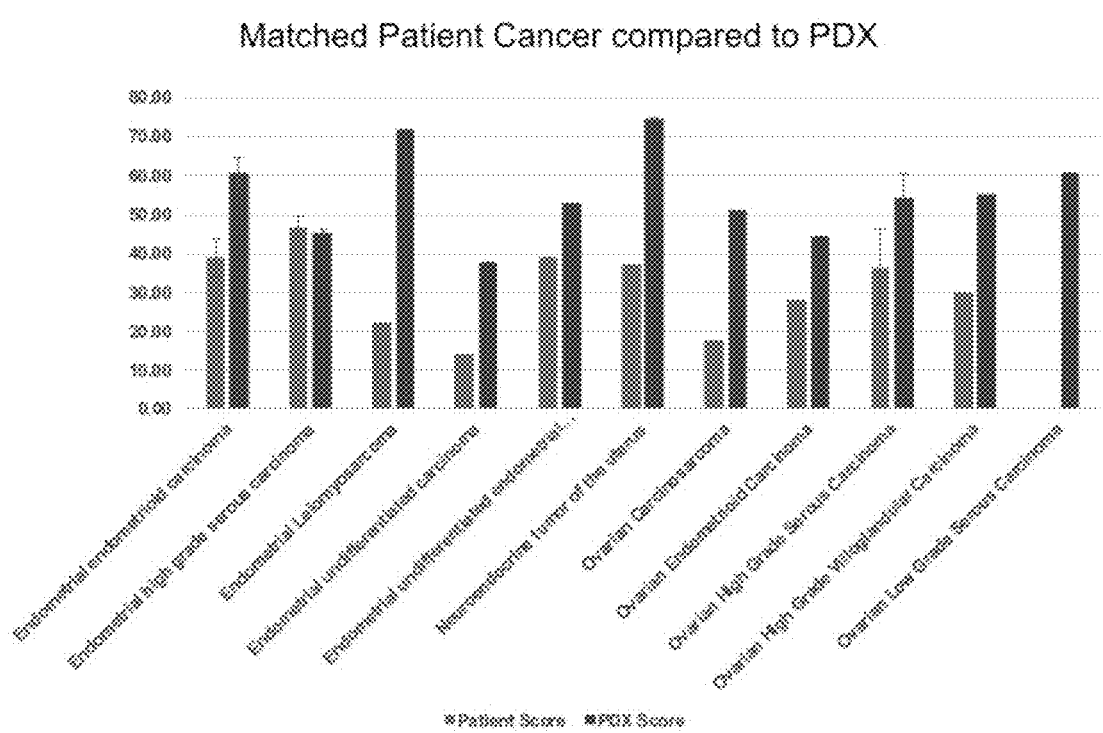
FIG. 13 illustrates a graph showing SBK-4 TR staining of matched patient cancer to PDX.

Patient Derived Xenograft Models have higher PTPµ Biomarker Staining than their Corresponding Original Patient Tumor Tissue We compared SBK4-TR staining of relevant normal tissue, tumor tissue and PDX tumors (FIG. 11). High-grade ovarian serous tumor had statistically significantly higher staining than relevant normal controls. High-grade serous ovarian carcinoma where tumor and PDX tissue was well matched. Our results indicate that for the rest of the tumor types, PDX tissue had higher levels of SBK4-TR labeling than the original patient tumor tissue. In addition to evaluating SBK4-TR labeling of tumor tissue sections in general, we also had a TMA to directly compare the level of SBK4-TR staining of an individual patient tumor sample and their matched PDX tumors (FIG. 12). Our results indicate that for all samples, PDX tissue had higher levels of SBK4-TR labeling than the original patient tumor tissue (FIG. 13).

In terms of biomarkers for HGSOC, the high level of TP53 mutations results in frequent immunoreactivity for nuclear p53 staining. This is true mostly for missense mutations, as nonsense mutations yield little to no staining (1). Other markers of HGSOC include WT-1, CDKN2A (p16), and CK7 (1). Other markers of epithelial ovarian cancers, such as estrogen and progesterone receptors can be found in 80% and 30% of cases, respectively. PAX8 is a typical marker of cells of Mullerian origin (1). The two mutations and thus markers shared by both gliomas and HGSOC are p53 and p16.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention, the following is claimed:

1. A method of determining a prognosis for a subject with a glioma, the method comprising:
    administering a probe to a glioma sample of the subject, the probe comprising a targeting agent that binds to a proteolytically cleaved extracellular fragment of PTPμ in the glioma sample, the targeting agent comprising a polypeptide that specifically binds to and/or complexes with the proteolytically cleaved extracellular fragment of PTPμ, and wherein the polypeptide comprises the amino acid sequence of SEQ ID NO: 7;
    measuring a level of the probe bound to and/or complexed with the proteolytically cleaved extracellular fragments of PTPμ of the glioma sample; and
    determining a prognosis for the subject with the glioma based on the measured level compared to a reference level of the probe bound to and/or complexed with the proteolytically cleaved extracellular fragments of PTPμ in a subject having the same glioma subtype, subgroup, stage, and/or grade as the subject for which the measured level is determined, wherein the measured level if elevated compared to the reference level is indicative of an increased likelihood of survival of the subject, and the measured level if below than the reference level is indicative of an increased likelihood of death of the subject.

2. The method of claim 1, the polypeptide homophilically binds to the extracellular fragment.

3. The method of claim 1, wherein the probe further includes a detectable moiety, the detectable moiety comprising at least one of ligands, radiolabels, fluorescent agents and dyes, infrared and near infrared agents, chemiluminescent agents, microparticles or nanoparticles, enzymes, colorimetric labels, magnetic labels, and chelating agents.

4. The method of claim 1, wherein the glioma is low grade glioma (LGG), high grade glioma (HGG), glioblastoma, or glioblastoma multiforme (GBM).

5. The method of claim 1, further comprising determining the presence of a mutation in IDH1/2 expressed by the glioma, wherein the presence of IDH1/2 mutations is indicative of increased likelihood of survival of the subject.

6. A method of determining survival of a subject with a glioma, the method comprising:
    administering a probe to a glioma sample of the subject, the probe comprising a targeting agent that binds to proteolytically cleaved extracellular fragments of PTPμ in the glioma sample, the targeting agent comprising a polypeptide that specifically binds to and/or complexes with the extracellular fragment of PTPμ, and wherein the polypeptide comprises the amino acid sequence of SEQ ID NO: 7;
    measuring a level of binding of the probe to the proteolytically cleaved extracellular fragments of PTPμ of the glioma sample obtained from the subject; and
    determining the survival of the subject based on the measured level compared to a reference level of the probe bound to and/or complexed with the proteolytically cleaved extracellular fragments of PTPμ in a subject having the same glioma subtype, subgroup, stage, and/or grade as the subject for which the measured level is determined, wherein the measured level if elevated compared to the reference level is indicative of an increased likelihood of survival of the subject and the measured level if below than the reference level is indicative of an increased likelihood of death of the subject.

7. The method of claim 6, wherein the probe further includes a detectable moiety, the detectable moiety comprising at least one of ligands, radiolabels, fluorescent agents and dyes, infrared and near infrared agents, chemiluminescent agents, microparticles or nanoparticles, enzymes, colorimetric labels, magnetic labels, and chelating agents.

8. The method of claim 6, wherein glioma is a low grade glioma (LGG), high grade glioma (HGG), glioblastoma, or glioblastoma multiforme (GBM).

9. The method of claim 6, further comprising determining the presence of a mutation in IDH1/2 expressed by the glioma, wherein the presence of IDH1/2 mutations is indicative of increased likelihood of survival of the subject.

* * * * *

SEQUENCE LISTING

<160> NUMBER OF SEQ ID NOS: 16

<210> SEQ ID NO 1
<211> LENGTH: 1465
<212> TYPE: PRT
<213> ORGANISM: Homo sapiens

<400> SEQUENCE: 1

Met Arg Gly Leu Gly Thr Cys Leu Ala Thr Leu Ala Gly Leu Leu Leu
1               5                   10                  15

Thr Ala Ala Gly Glu Thr Phe Ser Gly Gly Cys Leu Phe Asp Glu Pro
            20                  25                  30

Tyr Ser Thr Cys Gly Tyr Ser Gln Ser Glu Gly Asp Asp Phe Asn Trp
        35                  40                  45

Glu Gln Val Asn Thr Leu Thr Lys Pro Thr Ser Asp Pro Trp Met Pro
    50                  55                  60

Ser Gly Ser Phe Met Leu Val Asn Ala Ser Gly Arg Pro Glu Gly Gln
65                  70                  75                  80

Arg Ala His Leu Leu Leu Pro Gln Leu Lys Glu Asn Asp Thr His Cys
                85                  90                  95

Ile Asp Phe His Tyr Phe Val Ser Ser Lys Ser Asn Ser Pro Pro Gly
            100                 105                 110

Leu Leu Asn Val Tyr Val Lys Val Asn Asn Gly Pro Leu Gly Asn Pro
        115                 120                 125

Ile Trp Asn Ile Ser Gly Asp Pro Thr Arg Thr Trp Asn Arg Ala Glu
130                 135                 140

Leu Ala Ile Ser Thr Phe Trp Pro Asn Phe Tyr Gln Val Ile Phe Glu
145                 150                 155                 160

Val Ile Thr Ser Gly His Gln Gly Tyr Leu Ala Ile Asp Glu Val Lys
                165                 170                 175

Val Leu Gly His Pro Cys Thr Arg Thr Pro His Phe Leu Arg Ile Gln
            180                 185                 190

Asn Val Glu Val Asn Ala Gly Gln Phe Ala Thr Phe Gln Cys Ser Ala
        195                 200                 205

Ile Gly Arg Thr Val Ala Gly Asp Arg Leu Trp Leu Gln Gly Ile Asp
210                 215                 220

Val Arg Asp Ala Pro Leu Lys Glu Ile Lys Val Thr Ser Ser Arg Arg
225                 230                 235                 240

Phe Ile Ala Ser Phe Asn Val Val Asn Thr Thr Lys Arg Asp Ala Gly
                245                 250                 255

Lys Tyr Arg Cys Met Ile Arg Thr Glu Gly Gly Val Gly Ile Ser Asn
            260                 265                 270

Tyr Ala Glu Leu Val Val Lys Glu Pro Pro Val Pro Ile Ala Pro Pro
        275                 280                 285

Gln Leu Ala Ser Val Gly Ala Thr Tyr Leu Trp Ile Gln Leu Asn Ala
        290                 295                 300

Asn Ser Ile Asn Gly Asp Gly Pro Ile Val Ala Arg Glu Val Glu Tyr
305                 310                 315                 320

Cys Thr Ala Ser Gly Ser Trp Asn Asp Arg Gln Pro Val Asp Ser Thr
                325                 330                 335

Ser Tyr Lys Ile Gly His Leu Asp Pro Asp Thr Glu Tyr Glu Ile Ser
            340                 345                 350

Val Leu Leu Thr Arg Pro Gly Glu Gly Gly Thr Gly Ser Pro Gly Pro
        355                 360                 365

```
Ala Leu Arg Thr Arg Thr Lys Cys Ala Asp Pro Met Arg Gly Pro Arg
        370                 375                 380
Lys Leu Glu Val Glu Val Lys Ser Arg Gln Ile Thr Ile Arg Trp
385                 390                 395                 400
Glu Pro Phe Gly Tyr Asn Val Thr Arg Cys His Ser Tyr Asn Leu Thr
                    405                 410                 415
Val His Tyr Cys Tyr Gln Val Gly Gly Gln Glu Gln Val Arg Glu Glu
                420                 425                 430
Val Ser Trp Asp Thr Glu Asn Ser His Pro Gln His Thr Ile Thr Asn
            435                 440                 445
Leu Ser Pro Tyr Thr Asn Val Ser Val Lys Leu Ile Leu Met Asn Pro
450                 455                 460
Glu Gly Arg Lys Glu Ser Gln Glu Leu Ile Val Gln Thr Asp Glu Asp
465                 470                 475                 480
Leu Pro Gly Ala Val Pro Thr Glu Ser Ile Gln Gly Ser Thr Phe Glu
                485                 490                 495
Glu Lys Ile Phe Leu Gln Trp Arg Glu Pro Thr Gln Thr Tyr Gly Val
                500                 505                 510
Ile Thr Leu Tyr Glu Ile Thr Tyr Lys Ala Val Ser Ser Phe Asp Pro
            515                 520                 525
Glu Ile Asp Leu Ser Asn Gln Ser Gly Arg Val Ser Lys Leu Gly Asn
            530                 535                 540
Glu Thr His Phe Leu Phe Phe Gly Leu Tyr Pro Gly Thr Thr Tyr Ser
545                 550                 555                 560
Phe Thr Ile Arg Ala Ser Thr Ala Lys Gly Phe Gly Pro Pro Ala Thr
                565                 570                 575
Asn Gln Phe Thr Thr Lys Ile Ser Ala Pro Ser Met Pro Ala Tyr Glu
                580                 585                 590
Leu Glu Thr Pro Leu Asn Gln Thr Asp Asn Thr Val Thr Val Met Leu
                595                 600                 605
Lys Pro Ala His Ser Arg Gly Ala Pro Val Ser Val Tyr Gln Ile Val
610                 615                 620
Val Glu Glu Arg Pro Arg Arg Thr Lys Lys Thr Thr Glu Ile Leu
625                 630                 635                 640
Lys Cys Tyr Pro Val Pro Ile His Phe Gln Asn Ala Ser Leu Leu Asn
                645                 650                 655
Ser Gln Tyr Tyr Phe Ala Ala Glu Phe Pro Ala Asp Ser Leu Gln Ala
                660                 665                 670
Ala Gln Pro Phe Thr Ile Gly Asp Asn Lys Thr Tyr Asn Gly Tyr Trp
                675                 680                 685
Asn Thr Pro Leu Leu Pro Tyr Lys Ser Tyr Arg Ile Tyr Phe Gln Ala
690                 695                 700
Ala Ser Arg Ala Asn Gly Glu Thr Lys Ile Asp Cys Val Gln Val Ala
705                 710                 715                 720
Thr Lys Gly Ala Ala Thr Pro Lys Pro Val Pro Glu Pro Glu Lys Gln
                725                 730                 735
Thr Asp His Thr Val Lys Ile Ala Gly Val Ile Ala Gly Ile Leu Leu
                740                 745                 750
Phe Val Ile Ile Phe Leu Gly Val Val Leu Val Met Lys Lys Arg Lys
            755                 760                 765
Leu Ala Lys Lys Arg Lys Glu Thr Met Ser Ser Thr Arg Gln Glu Met
770                 775                 780
Thr Val Met Val Asn Ser Met Asp Lys Ser Tyr Ala Glu Gln Gly Thr
```

-continued

```
                785                 790                 795                 800
Asn Cys Asp Glu Ala Phe Ser Phe Met Asp Thr His Asn Leu Asn Gly
                    805                 810                 815
Arg Ser Val Ser Ser Pro Ser Ser Phe Thr Met Lys Thr Asn Thr Leu
                    820                 825                 830
Ser Thr Ser Val Pro Asn Ser Tyr Tyr Pro Asp Pro Phe Val Pro Thr
                    835                 840                 845
Ala Ile Leu Val Pro Ile Asn Asp Glu Thr His Thr Met Ala Ser Asp
                    850                 855                 860
Thr Ser Ser Leu Val Gln Ser His Thr Tyr Lys Lys Arg Glu Pro Ala
865                 870                 875                 880
Asp Val Pro Tyr Gln Thr Gly Gln Leu His Pro Ala Ile Arg Val Ala
                    885                 890                 895
Asp Leu Leu Gln His Ile Thr Gln Met Lys Cys Ala Glu Gly Tyr Gly
                    900                 905                 910
Phe Lys Glu Glu Tyr Glu Ser Phe Phe Glu Gly Gln Ser Ala Pro Trp
                    915                 920                 925
Asp Ser Ala Lys Lys Asp Glu Asn Arg Met Lys Asn Arg Tyr Gly Asn
930                 935                 940
Ile Ile Ala Tyr Asp His Ser Arg Val Arg Leu Gln Thr Ile Glu Gly
945                 950                 955                 960
Asp Thr Asn Ser Asp Tyr Ile Asn Gly Asn Tyr Ile Asp Gly Tyr His
                    965                 970                 975
Arg Pro Asn His Tyr Ile Ala Thr Gln Gly Pro Met Gln Glu Thr Ile
                    980                 985                 990
Tyr Asp Phe Trp Arg Met Val Trp His Glu Asn Thr Ala Ser Ile Ile
                    995                 1000                1005
Met Val Thr Asn Leu Val Glu Val Gly Arg Val Lys Cys Cys Lys
                    1010                1015                1020
Tyr Trp Pro Asp Asp Thr Glu Ile Tyr Lys Asp Ile Lys Val Thr
                    1025                1030                1035
Leu Ile Glu Thr Glu Leu Leu Ala Glu Tyr Val Ile Arg Thr Phe
                    1040                1045                1050
Ala Val Glu Lys Arg Gly Val His Glu Ile Arg Glu Ile Arg Gln
                    1055                1060                1065
Phe His Phe Thr Gly Trp Pro Asp His Gly Val Pro Tyr His Ala
                    1070                1075                1080
Thr Gly Leu Leu Gly Phe Val Arg Gln Val Lys Ser Lys Ser Pro
                    1085                1090                1095
Pro Ser Ala Gly Pro Leu Val Val His Cys Ser Ala Gly Ala Gly
                    1100                1105                1110
Arg Thr Gly Cys Phe Ile Val Ile Asp Ile Met Leu Asp Met Ala
                    1115                1120                1125
Glu Arg Glu Gly Val Val Asp Ile Tyr Asn Cys Val Arg Glu Leu
                    1130                1135                1140
Arg Ser Arg Arg Val Asn Met Val Gln Thr Glu Glu Gln Tyr Val
                    1145                1150                1155
Phe Ile His Asp Ala Ile Leu Glu Ala Cys Leu Cys Gly Asp Thr
                    1160                1165                1170
Ser Val Pro Ala Ser Gln Val Arg Ser Leu Tyr Tyr Asp Met Asn
                    1175                1180                1185
Lys Leu Asp Pro Gln Thr Asn Ser Ser Gln Ile Lys Glu Glu Phe
                    1190                1195                1200
```

```
Arg Thr Leu Asn Met Val Thr Pro Thr Leu Arg Val Glu Asp Cys
    1205                1210                1215

Ser Ile Ala Leu Leu Pro Arg Asn His Glu Lys Asn Arg Cys Met
    1220                1225                1230

Asp Ile Leu Pro Pro Asp Arg Cys Leu Pro Phe Leu Ile Thr Ile
    1235                1240                1245

Asp Gly Glu Ser Ser Asn Tyr Ile Asn Ala Ala Leu Met Asp Ser
    1250                1255                1260

Tyr Lys Gln Pro Ser Ala Phe Ile Val Thr Gln His Pro Leu Pro
    1265                1270                1275

Asn Thr Val Lys Asp Phe Trp Arg Leu Val Leu Asp Tyr His Cys
    1280                1285                1290

Thr Ser Val Val Met Leu Asn Asp Val Asp Pro Ala Gln Leu Cys
    1295                1300                1305

Pro Gln Tyr Trp Leu Glu Asn Gly Val His Arg His Gly Pro Ile
    1310                1315                1320

Gln Val Glu Phe Val Ser Ala Asp Leu Glu Glu Asp Ile Ile Ser
    1325                1330                1335

Arg Ile Phe Arg Ile Tyr Asn Ala Ala Arg Pro Gln Asp Gly Tyr
    1340                1345                1350

Arg Met Val Gln Gln Phe Gln Phe Leu Gly Trp Pro Met Tyr Arg
    1355                1360                1365

Asp Thr Pro Val Ser Lys Arg Ser Phe Leu Lys Leu Ile Arg Gln
    1370                1375                1380

Val Asp Lys Trp Gln Glu Glu Tyr Asn Gly Gly Glu Gly Arg Thr
    1385                1390                1395

Val Val His Cys Leu Asn Gly Gly Gly Arg Ser Gly Thr Phe Cys
    1400                1405                1410

Ala Ile Ser Ile Val Cys Glu Met Leu Arg His Gln Arg Thr Val
    1415                1420                1425

Asp Val Phe His Ala Val Lys Thr Leu Arg Asn Asn Lys Pro Asn
    1430                1435                1440

Met Val Asp Leu Leu Asp Gln Tyr Lys Phe Cys Tyr Glu Val Ala
    1445                1450                1455

Leu Glu Tyr Leu Asn Ser Gly
    1460                1465

<210> SEQ ID NO 2
<211> LENGTH: 477
<212> TYPE: PRT
<213> ORGANISM: Homo sapiens

<400> SEQUENCE: 2

Met Arg Gly Leu Gly Thr Cys Leu Ala Thr Leu Ala Gly Leu Leu Leu
1               5                   10                  15

Thr Ala Ala Gly Glu Thr Phe Ser Gly Gly Cys Leu Phe Asp Glu Pro
                20                  25                  30

Tyr Ser Thr Cys Gly Tyr Ser Gln Ser Glu Gly Asp Asp Phe Asn Trp
            35                  40                  45

Glu Gln Val Asn Thr Leu Thr Lys Pro Thr Ser Asp Pro Trp Met Pro
        50                  55                  60

Ser Gly Ser Phe Met Leu Val Asn Ala Ser Gly Arg Pro Glu Gly Gln
65                  70                  75                  80

Arg Ala His Leu Leu Leu Pro Gln Leu Lys Glu Asn Asp Thr His Cys
```

```
                        85                  90                  95
Ile Asp Phe His Tyr Phe Val Ser Ser Lys Ser Asn Ser Pro Pro Gly
                    100                 105                 110

Leu Leu Asn Val Tyr Val Lys Val Asn Asn Gly Pro Leu Gly Asn Pro
                115                 120                 125

Ile Trp Asn Ile Ser Gly Asp Pro Thr Arg Thr Trp Asn Arg Ala Glu
            130                 135                 140

Leu Ala Ile Ser Thr Phe Trp Pro Asn Phe Tyr Gln Val Ile Phe Glu
145                 150                 155                 160

Val Ile Thr Ser Gly His Gln Gly Tyr Leu Ala Ile Asp Glu Val Lys
                165                 170                 175

Val Leu Gly His Pro Cys Thr Arg Thr Pro His Phe Leu Arg Ile Gln
                180                 185                 190

Asn Val Glu Val Asn Ala Gly Gln Phe Ala Thr Phe Gln Cys Ser Ala
                195                 200                 205

Ile Gly Arg Thr Val Ala Gly Asp Arg Leu Trp Leu Gln Gly Ile Asp
            210                 215                 220

Val Arg Asp Ala Pro Leu Lys Glu Ile Lys Val Thr Ser Ser Arg Arg
225                 230                 235                 240

Phe Ile Ala Ser Phe Asn Val Asn Thr Thr Lys Arg Asp Ala Gly
                245                 250                 255

Lys Tyr Arg Cys Met Ile Arg Thr Glu Gly Val Gly Ile Ser Asn
                260                 265                 270

Tyr Ala Glu Leu Val Val Lys Glu Pro Pro Val Pro Ile Ala Pro Pro
                275                 280                 285

Gln Leu Ala Ser Val Gly Ala Thr Tyr Leu Trp Ile Gln Leu Asn Ala
            290                 295                 300

Asn Ser Ile Asn Gly Asp Gly Pro Ile Val Ala Arg Glu Val Glu Tyr
305                 310                 315                 320

Cys Thr Ala Ser Gly Ser Trp Asn Asp Arg Gln Pro Val Asp Ser Thr
                325                 330                 335

Ser Tyr Lys Ile Gly His Leu Asp Pro Asp Thr Glu Tyr Glu Ile Ser
                340                 345                 350

Val Leu Leu Thr Arg Pro Gly Glu Gly Gly Thr Gly Ser Pro Gly Pro
            355                 360                 365

Ala Leu Arg Thr Arg Thr Lys Cys Ala Asp Pro Met Arg Gly Pro Arg
            370                 375                 380

Lys Leu Glu Val Val Glu Val Lys Ser Arg Gln Ile Thr Ile Arg Trp
385                 390                 395                 400

Glu Pro Phe Gly Tyr Asn Val Thr Arg Cys His Ser Tyr Asn Leu Thr
                405                 410                 415

Val His Tyr Cys Tyr Gln Val Gly Gly Gln Glu Gln Val Arg Glu Glu
                420                 425                 430

Val Ser Trp Asp Thr Glu Asn Ser His Pro Gln His Thr Ile Thr Asn
            435                 440                 445

Leu Ser Pro Tyr Thr Asn Val Ser Val Lys Leu Ile Leu Met Asn Pro
450                 455                 460

Glu Gly Arg Lys Glu Ser Gln Glu Leu Ile Val Gln Thr
465                 470                 475

<210> SEQ ID NO 3
<211> LENGTH: 280
<212> TYPE: PRT
<213> ORGANISM: Homo sapiens
```

<400> SEQUENCE: 3

```
Met Arg Gly Leu Gly Thr Cys Leu Ala Thr Leu Ala Gly Leu Leu Leu
1               5                   10                  15

Thr Ala Ala Gly Glu Thr Phe Ser Gly Gly Cys Leu Phe Asp Glu Pro
                20                  25                  30

Tyr Ser Thr Cys Gly Tyr Ser Gln Ser Glu Gly Asp Asp Phe Asn Trp
            35                  40                  45

Glu Gln Val Asn Thr Leu Thr Lys Pro Thr Ser Asp Pro Trp Met Pro
    50                  55                  60

Ser Gly Ser Phe Met Leu Val Asn Ala Ser Gly Arg Pro Glu Gly Gln
65                  70                  75                  80

Arg Ala His Leu Leu Leu Pro Gln Leu Lys Glu Asn Asp Thr His Cys
                85                  90                  95

Ile Asp Phe His Tyr Phe Val Ser Ser Lys Ser Asn Ser Pro Pro Gly
            100                 105                 110

Leu Leu Asn Val Tyr Val Lys Val Asn Asn Gly Pro Leu Gly Asn Pro
        115                 120                 125

Ile Trp Asn Ile Ser Gly Asp Pro Thr Arg Thr Trp Asn Arg Ala Glu
130                 135                 140

Leu Ala Ile Ser Thr Phe Trp Pro Asn Phe Tyr Gln Val Ile Phe Glu
145                 150                 155                 160

Val Ile Thr Ser Gly His Gln Gly Tyr Leu Ala Ile Asp Glu Val Lys
                165                 170                 175

Val Leu Gly His Pro Cys Thr Arg Thr Pro His Phe Leu Arg Ile Gln
            180                 185                 190

Asn Val Glu Val Asn Ala Gly Gln Phe Ala Thr Phe Gln Cys Ser Ala
        195                 200                 205

Ile Gly Arg Thr Val Ala Gly Asp Arg Leu Trp Leu Gln Gly Ile Asp
210                 215                 220

Val Arg Asp Ala Pro Leu Lys Glu Ile Lys Val Thr Ser Ser Arg Arg
225                 230                 235                 240

Phe Ile Ala Ser Phe Asn Val Val Asn Thr Thr Lys Arg Asp Ala Gly
                245                 250                 255

Lys Tyr Arg Cys Met Ile Arg Thr Glu Gly Gly Val Gly Ile Ser Asn
            260                 265                 270

Tyr Ala Glu Leu Val Val Lys Glu
        275                 280
```

<210> SEQ ID NO 4
<211> LENGTH: 20
<212> TYPE: PRT
<213> ORGANISM: Artificial Sequence
<220> FEATURE:
<223> OTHER INFORMATION: Synthetic peptide

<400> SEQUENCE: 4

```
Glu Thr Phe Ser Gly Gly Cys Leu Phe Asp Glu Pro Tyr Ser Thr Cys
1               5                   10                  15

Gly Tyr Ser Gln
            20
```

<210> SEQ ID NO 5
<211> LENGTH: 20
<212> TYPE: PRT
<213> ORGANISM: Artificial Sequence
<220> FEATURE:

```
<223> OTHER INFORMATION: Synthetic peptide

<400> SEQUENCE: 5

Gly Glu Gly Asp Asp Phe Asn Trp Glu Gln Val Asn Thr Leu Thr Lys
1               5                   10                  15

Pro Thr Ser Asp
            20

<210> SEQ ID NO 6
<211> LENGTH: 19
<212> TYPE: PRT
<213> ORGANISM: Artificial Sequence
<220> FEATURE:
<223> OTHER INFORMATION: Synthetic peptide

<400> SEQUENCE: 6

Thr Pro His Phe Leu Arg Ile Gln Asn Val Glu Val Asn Ala Gly Gln
1               5                   10                  15

Phe Ala Thr

<210> SEQ ID NO 7
<211> LENGTH: 18
<212> TYPE: PRT
<213> ORGANISM: Artificial Sequence
<220> FEATURE:
<223> OTHER INFORMATION: Synthetic peptide

<400> SEQUENCE: 7

Gly Ile Asp Val Arg Asp Ala Pro Leu Lys Glu Ile Lys Val Thr Ser
1               5                   10                  15

Ser Arg

<210> SEQ ID NO 8
<211> LENGTH: 21
<212> TYPE: PRT
<213> ORGANISM: Artificial Sequence
<220> FEATURE:
<223> OTHER INFORMATION: Synthetic Construct

<400> SEQUENCE: 8

Cys Gly Glu Gly Asp Asp Phe Asn Trp Glu Gln Val Asn Thr Leu Thr
1               5                   10                  15

Lys Pro Thr Ser Asp
            20

<210> SEQ ID NO 9
<211> LENGTH: 23
<212> TYPE: PRT
<213> ORGANISM: Artificial Sequence
<220> FEATURE:
<223> OTHER INFORMATION: Synthetic Construct

<400> SEQUENCE: 9

Gly Gly Gly Gly Glu Gly Asp Asp Phe Asn Trp Glu Gln Val Asn Thr
1               5                   10                  15

Leu Thr Lys Pro Thr Ser Asp
            20

<210> SEQ ID NO 10
<211> LENGTH: 26
<212> TYPE: PRT
<213> ORGANISM: Artificial Sequence
<220> FEATURE:
<223> OTHER INFORMATION: Synthetic Construct
```

```
<400> SEQUENCE: 10

Gly Gly Gly Gly Gly Gly Gly Glu Gly Asp Asp Phe Asn Trp Glu Gln
1               5                   10                  15

Val Asn Thr Leu Thr Lys Pro Thr Ser Asp
            20                  25

<210> SEQ ID NO 11
<211> LENGTH: 26
<212> TYPE: PRT
<213> ORGANISM: Artificial Sequence
<220> FEATURE:
<223> OTHER INFORMATION: Synthetic Construct

<400> SEQUENCE: 11

Gly Gly Ser Gly Gly Ser Gly Glu Gly Asp Asp Phe Asn Trp Glu Gln
1               5                   10                  15

Val Asn Thr Leu Thr Lys Pro Thr Ser Asp
            20                  25

<210> SEQ ID NO 12
<211> LENGTH: 26
<212> TYPE: PRT
<213> ORGANISM: Artificial Sequence
<220> FEATURE:
<223> OTHER INFORMATION: Synthetic Construct

<400> SEQUENCE: 12

Gly Ser Gly Ser Gly Ser Gly Glu Gly Asp Asp Phe Asn Trp Glu Gln
1               5                   10                  15

Val Asn Thr Leu Thr Lys Pro Thr Ser Asp
            20                  25

<210> SEQ ID NO 13
<211> LENGTH: 21
<212> TYPE: PRT
<213> ORGANISM: Artificial Sequence
<220> FEATURE:
<223> OTHER INFORMATION: Synthetic Construct

<400> SEQUENCE: 13

Gly Gly Gly Gly Ile Asp Val Arg Asp Ala Pro Leu Lys Glu Ile Lys
1               5                   10                  15

Val Thr Ser Ser Arg
            20

<210> SEQ ID NO 14
<211> LENGTH: 24
<212> TYPE: PRT
<213> ORGANISM: Artificial Sequence
<220> FEATURE:
<223> OTHER INFORMATION: Synthetic Construct

<400> SEQUENCE: 14

Gly Gly Gly Gly Gly Gly Gly Ile Asp Val Arg Asp Ala Pro Leu Lys
1               5                   10                  15

Glu Ile Lys Val Thr Ser Ser Arg
            20

<210> SEQ ID NO 15
<211> LENGTH: 24
<212> TYPE: PRT
<213> ORGANISM: Artificial Sequence
<220> FEATURE:
```

```
<223> OTHER INFORMATION: Synthetic Construct

<400> SEQUENCE: 15

Gly Gly Ser Gly Gly Ser Gly Ile Asp Val Arg Asp Ala Pro Leu Lys
1               5                   10                  15

Glu Ile Lys Val Thr Ser Ser Arg
            20

<210> SEQ ID NO 16
<211> LENGTH: 24
<212> TYPE: PRT
<213> ORGANISM: Artificial Sequence
<220> FEATURE:
<223> OTHER INFORMATION: Synthetic Construct

<400> SEQUENCE: 16

Gly Ser Gly Ser Gly Ser Gly Ile Asp Val Arg Asp Ala Pro Leu Lys
1               5                   10                  15

Glu Ile Lys Val Thr Ser Ser Arg
            20
```